US008267927B2

(12) United States Patent  
Dalal et al.

(10) Patent No.: US 8,267,927 B2
(45) Date of Patent: Sep. 18, 2012

(54) ADVANCED ABLATION PLANNING

(75) Inventors: Sandeep Dalal, Cortlandt Manor, NY (US); Karen Irene Trovato, Putnam Valley, NY (US); Jurgen Jan Rusch, Eindhoven (NL); Jochen Kruecker, Washington, DC (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 440 days.

(21) Appl. No.: 12/709,542

(22) Filed: Feb. 22, 2010

(65) Prior Publication Data

US 2011/0015628 A1   Jan. 20, 2011

Related U.S. Application Data

(63) Continuation-in-part of application No. 12/523,163, filed on Jul. 15, 2009.

(60) Provisional application No. 60/886,421, filed on Jan. 24, 2007.

(51) Int. Cl.
  *A61B 18/12*  (2006.01)
(52) U.S. Cl. ............................. 606/34; 606/41
(58) Field of Classification Search .............. 606/32–35, 606/41, 45–50
  See application file for complete search history.

(56) References Cited

U.S. PATENT DOCUMENTS

| | | | |
|---|---|---|---|
| 6,139,544 A | 10/2000 | Mikus et al. | |
| 6,358,245 B1 * | 3/2002 | Edwards et al. | 606/34 |
| 6,530,922 B2 * | 3/2003 | Cosman et al. | 606/34 |
| 6,575,969 B1 | 6/2003 | Rittman, III et al. | |
| 8,025,622 B2 * | 9/2011 | Rold et al. | 600/463 |
| 8,048,069 B2 * | 11/2011 | Skwarek et al. | 606/38 |
| 2003/0171672 A1 | 9/2003 | Varghese et al. | |
| 2004/0220562 A1 | 11/2004 | Garabedian et al. | |
| 2005/0041843 A1 | 2/2005 | Sawyer | |
| 2006/0089624 A1 * | 4/2006 | Voegele et al. | 606/1 |

FOREIGN PATENT DOCUMENTS

EP    1791070 A2    5/2007

OTHER PUBLICATIONS

Kalkofen, D., et al.; Integrated Surgical Workflow for Augmented Reality Applications; 2006; http://mustang.icg.tu-graz.ac.at/publ/ami-.

Wood, B. J., et al.; Technologies for guidance of Radiofrequency Ablation in the Multimodality Interventional suite of the Future; 2007; Journal of Vascular and Interventional Radiology; 18(1)9-24.

Perlin, K., et al.; Hypertexture; 1989; Computer Graphics; 23(3)253-261.

* cited by examiner

*Primary Examiner* — Michael Peffley

(57) ABSTRACT

In planning an ablation procedure, a planned target volume (PTV) is imported, which is typically selected by a doctor but may be computer-identified. An ablation solution comprising a plurality of ablation volumes is generated or selected using a lookup table. Ablations sharing a common axis along a line of insertion are grouped into blocks. Alternatively, the PTV is enveloped in a sphere, and a pre-computed ablation solution (e.g., a 6- or 14-sphere solution) is identified to cover the PTV sphere. Optionally, a mathematical algorithm is executed to increase an axis through the ablation spheres to generate ellipsoidal ablation volumes that envelop the PTV.

18 Claims, 17 Drawing Sheets

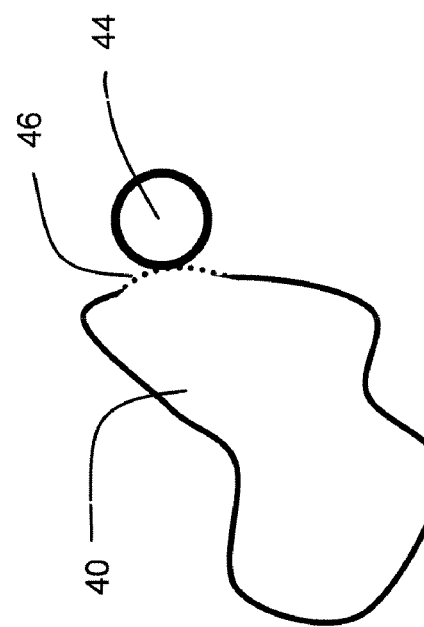
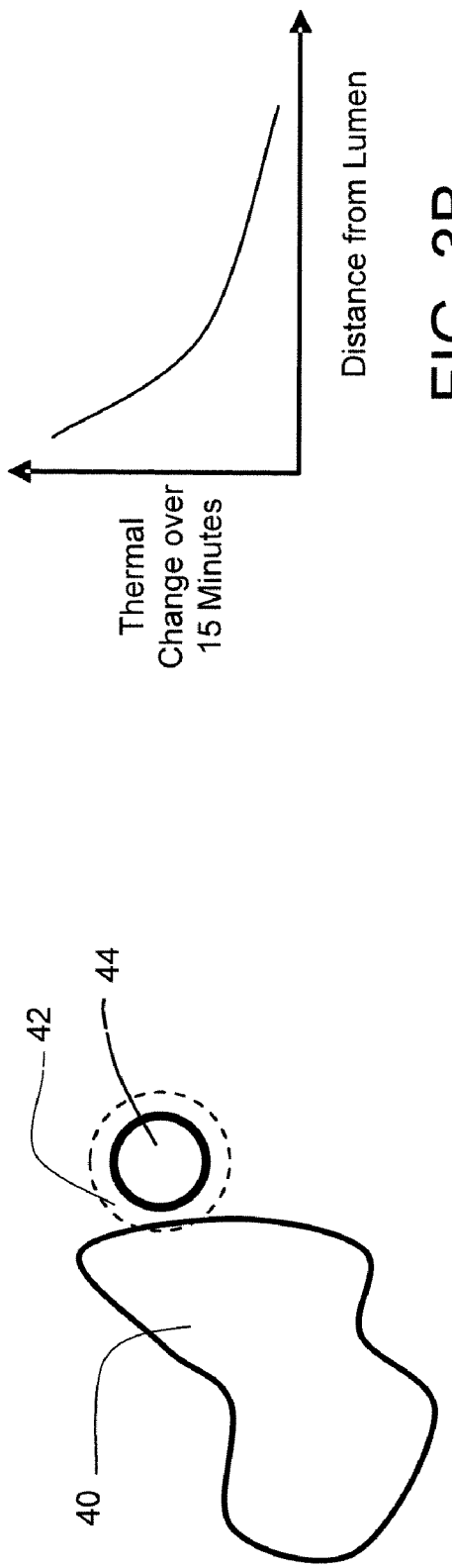

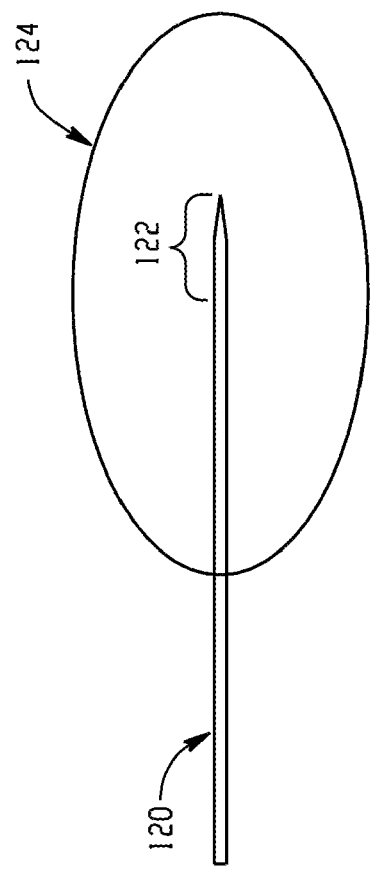
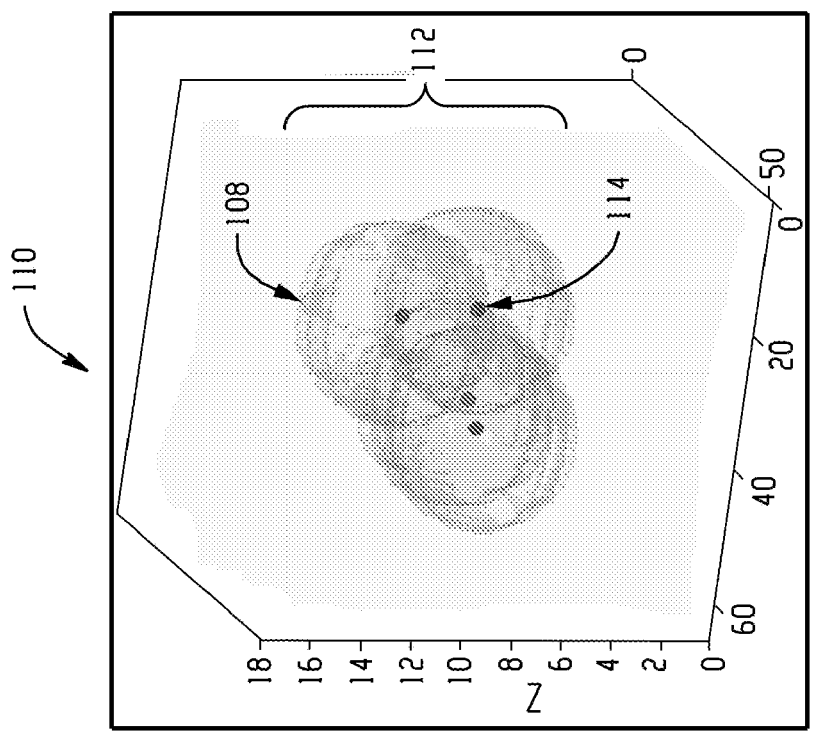
FIG. 8
FIG. 7

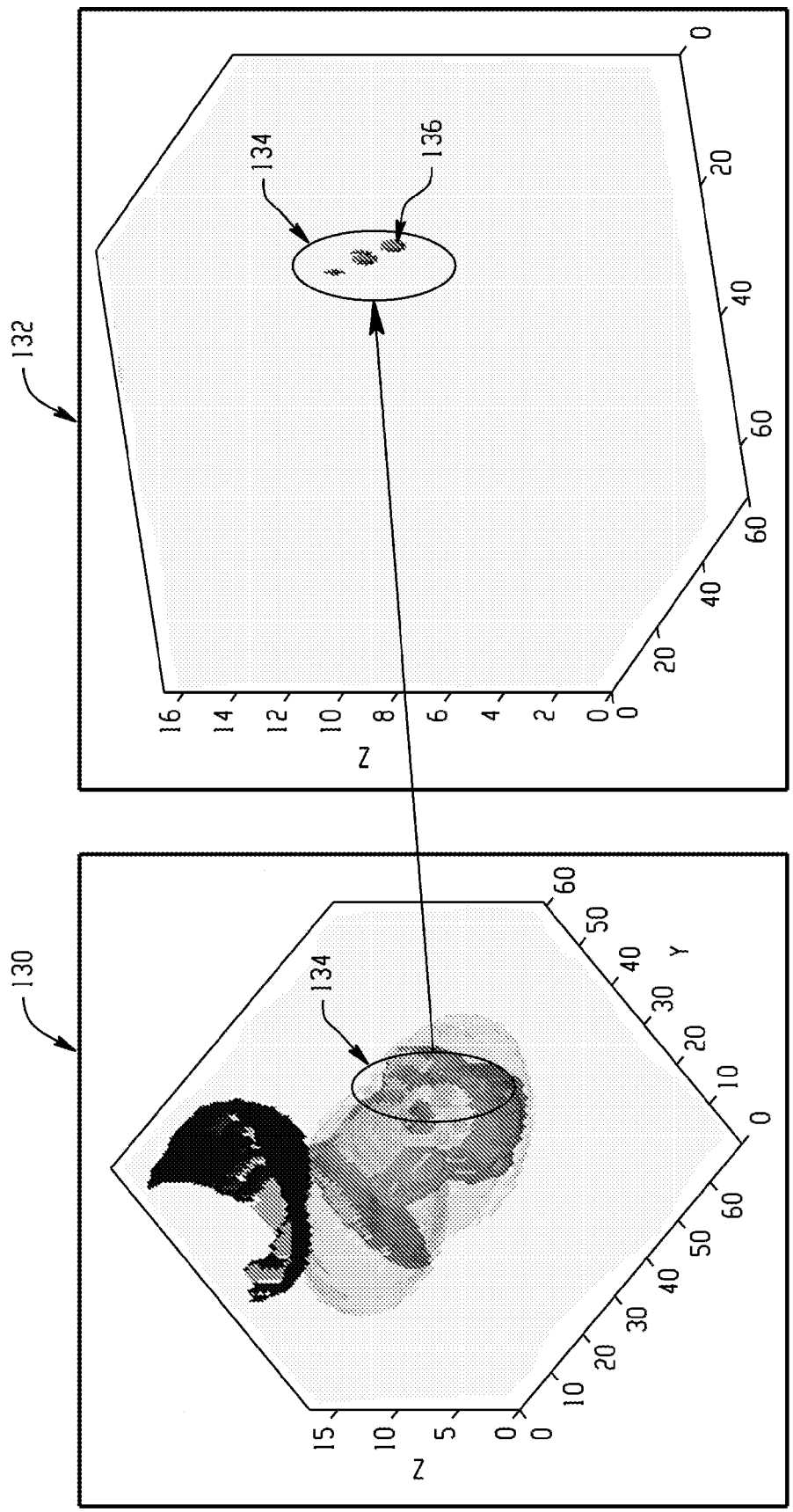

ADVANCED ABLATION PLANNING

CROSS REFERENCE TO RELATED APPLICATIONS

This application is a continuation-in-part of U.S. patent application Ser. No. 12/523,163 filed Jul. 15, 2009 which claims the benefit of U.S. provisional application Ser. No. 60/886,421 filed Jan. 24, 2007, which are incorporated herein by reference.

DESCRIPTION

The present application relates to radio frequency ablation (RFA), particularly involving inserting an RF electrode "probe" into a patient such that an expected ablation zone covers and kills a tumor by raising its temperature. However, it will be appreciated that the described technique may also find application in other ablation techniques, other surgical techniques or other radiation therapy techniques.

A probe may be connected to power for a predetermined time period (e.g., approximately 15 minutes, or some other suitable time period), and ablates in a variety of shapes, but commonly a sphere or ellipsoid. Currently, a physician may make a mental note about a location of a lesion to be ablated and may insert the probe utilizing various types of image guidance. Because probes are very expensive, a physician is deterred from using multiple probe sizes or configurations, in favor of attempting to ablate a tissue mass using a minimum number of probes.

When a tumor or lesion exceeds a size that cannot be successfully covered by a single ablation, treatment success rate drops dramatically. A margin around the tumor, often 1 cm, may be considered necessary in order to kill microscopic cancer cells. Leaving any portion of the tumor untreated can result in a recurrence, often an aggressive recurrence. Moreover, determining coverage of the tumor involves complex 3D geometric calculations and visualization which can be difficult for even the best of physicians. Still furthermore, each additional ablation adds to surgical and anesthesia time and cost and increases risk to the patient.

Other difficulties that can arise relate to complicated mental visualization of a single target location in 3D-space, and difficulty in controlling a probe so that it accurately reaches the target location, which adds additional potential for error. Additionally, ablation shapes often do not match the shape or size of the tumor, causing ablation of healthy tissue surrounding the tumor. The tumor may also be comprised of two or more smaller tumor regions that are not geometrically connected, but near enough to each other so that they should be treated together. Ablations may also damage 'critical regions' that can cause serious injury to the patient. Probe entry angles are typically chosen because they match the imaging system rather than because they minimize the number of ablations or reduce procedure risk. Furthermore, since each physician mentally creates a picture and plan, and manually directs the probe, there is no chance for repeatability, which is an important aspect of "evidence based medicine."

Ablation procedures such as radiofrequency ablation (RFA) or cryo-ablation have been performed in increasing numbers in recent years as an alternative to more invasive surgical procedures. During RFA, an electrode with un-insulated tip is inserted into the tumor or lesion to be ablated under ultrasound, CT or MRI guidance. When the electrode is placed, a radiofrequency current is applied to the tip which creates tissue heating and cell death above 60° Celsius. In order to destroy tumors that are larger than the volume around the needle tip that is heated and destroyed in a single treatment procedure, the needle tip needs to be repeatedly repositioned to ablate different parts of the tumor, partly overlapping with one another. This process needs to be repeated until the entire tumor is "covered" by the set of ablations, also referred to as the "composite ablation". Covering the entire tumor is important to lessen the risk of recurrence.

Currently, these composite ablations are performed without quantitative or computerized planning and depend on the intuition and experience of the physician. The process of composite ablation planning is difficult, and it has been pointed out that full coverage of a PTV with (smaller) individual ablations generally requires a surprisingly large number of ablations (See, e.g., Radiofrequency Thermal Ablation: Computer Analysis of the Size of the Thermal Injury Created by Overlapping Ablations, Dodd, et al., AJR 177, October, 2001). Thus, there is no guarantee that a "mentally planned" composite ablation actually fully covers the PTV, or that it covers the PTV in an optimal fashion, i.e. with the minimum number of ablations, and with minimal collateral damage to healthy tissue.

Another approach is described in Khajanchee ("A Mathematical Model for Preoperative Planning of Radiofrequency Ablation of Hepatic Tumors," Surg Endosc (2004), 18:696-701), which is hereby incorporated by reference in its entirety. Khajanchee discusses coverage of a "Target Sphere" with "Ablation Spheres." The larger target sphere is covered by ablation spheres by first identifying a regular polyhedron that fits tightly within a circumscribing sphere the size of the Target Sphere. The center of each polygonal face defines the center of each ablation sphere. This technique recommends using face-centers of 4-, 6-, and 12-sided regular polyhedra (tetrahedron, cube, dodecahedron), as well as 26- and 32-sided semi-regular polyhedra (e.g., rhombicubeoctahedron and truncated icosahedron).

The present application provides new and improved tumor ablation systems and methods, which overcome the above-referenced problems and others.

In accordance with one aspect, a method for planning an ablation procedure to eliminate a tissue mass in a patient includes identifying a tissue mass in the patient, generating an image representation of an initial planned target volume (PTV) encompassing the tissue mass, and inscribing the initial PTV in a template ellipsoidal enclosing ablation volume. The method further includes scaling minor axes of the template ellipsoidal enclosing ablation volume and the initial PTV upward until they are equal in magnitude to a major axis of the template ellipsoidal enclosing ablation volume, to generate an enclosing sphere that encompasses the scaled PTV. Additionally, the method includes identifying in a lookup table a pre-computed ablation solution having a minimum number of spherical ablation regions that cover the enclosing sphere, and outputting to a user a graphical representation of the identified precomputed ablation solution overlaid on the sphere.

In another aspect, a method for planning an ablation procedure to eliminate a tissue mass in a patient includes identifying a tissue mass in the patient, generating an image representation of an initial planned target volume (PTV) encompassing the tissue mass, and selecting a bounding polyhedron as a function of a tumor-to-ablation (TA) factor that describes a relationship between radius of a known ellipsoidal ablation volume radius and radius of the PTV. The method further includes positioning the bounding polyhedron around the PTV, positioning an ellipsoidal ablation volume in the bounding polyhedron such that a center of the ellipsoidal ablation volume coincides with a center of the bounding polyhedron, and increasing the TA factor by which axes of the ellipsoidal ablation volume are multiplied until the axes are equal to or greater than corresponding dimensions of the bounding polyhedron. The method additionally includes identifying in a lookup table a pre-computed ablation solution having a minimum number of spherical ablation regions that cover the enclosing sphere, and outputting to a user a graphical representation of the identified precomputed ablation solution overlaid on the scaled PTV.

In another aspect, a system for planning an ablation procedure for ablation of a tissue mass in a patient includes a graphical user interface that presents a representation of the tissue mass to a user, and an optimization component that generates a planned target volume (PTV), which includes the tissue mass, receives image data related to the tissue mass, and generates an enclosing ellipsoid ablation volume that encompasses the PTV. The optimization component furthermore identifies a polyhedron shape that encompasses the enclosing ellipsoid, identifies a plurality of spheroid ablation regions to cover the enclosing ellipsoid having respective centroids positioned on centers respective sides of the polyhedron shape, executes a mathematical algorithm to lengthen an axis of the spherical ablation regions to form ellipsoid ablation regions therefrom, and outputs graphical information to the user displaying the ellipsoid ablation regions overlaid on the PTV.

In another aspect, a method of planning an ablation procedure to eliminate a tissue mass in a patient includes identifying a tissue mass in the patient, generating an image representation of an initial planned target volume (PTV) encompassing the tissue mass, and performing a pilot ablation using a selected ablation probe. The method further includes determining a shape of an ablation volume generated during the pilot ablation, and generating an ablation solution comprising a plurality of ablation volumes having the determined shape to cover the PTV.

One advantage is that critical regions (e.g., bone, bowel or the like) that are within an ablation region may be identified, and actions may be taken to avoid ablation thereof.

Another advantage resides in minimizing surgery duration.

Another advantage resides in accurately matching the ablation volume to the target.

Another advantage is that specific, quantitative target locations and orientations are determined. These specific values can be used to guide the physician with tracking devices, such as electro-magnetic trackers. They may also be used to control other devices such as robots, which require quantitative data.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating various aspects and are not to be construed as limiting the invention.

FIGS. 3A-C show an example PTV, near the aorta, and a graph of the resulting change in temperature as a function of the distance from the lumen of the aorta.

FIGS. 4A-D illustrate a plurality of graphical representations of various actions associated with planning an ablation procedure for a patient with an otherwise inoperable tumor.

Figure 5:
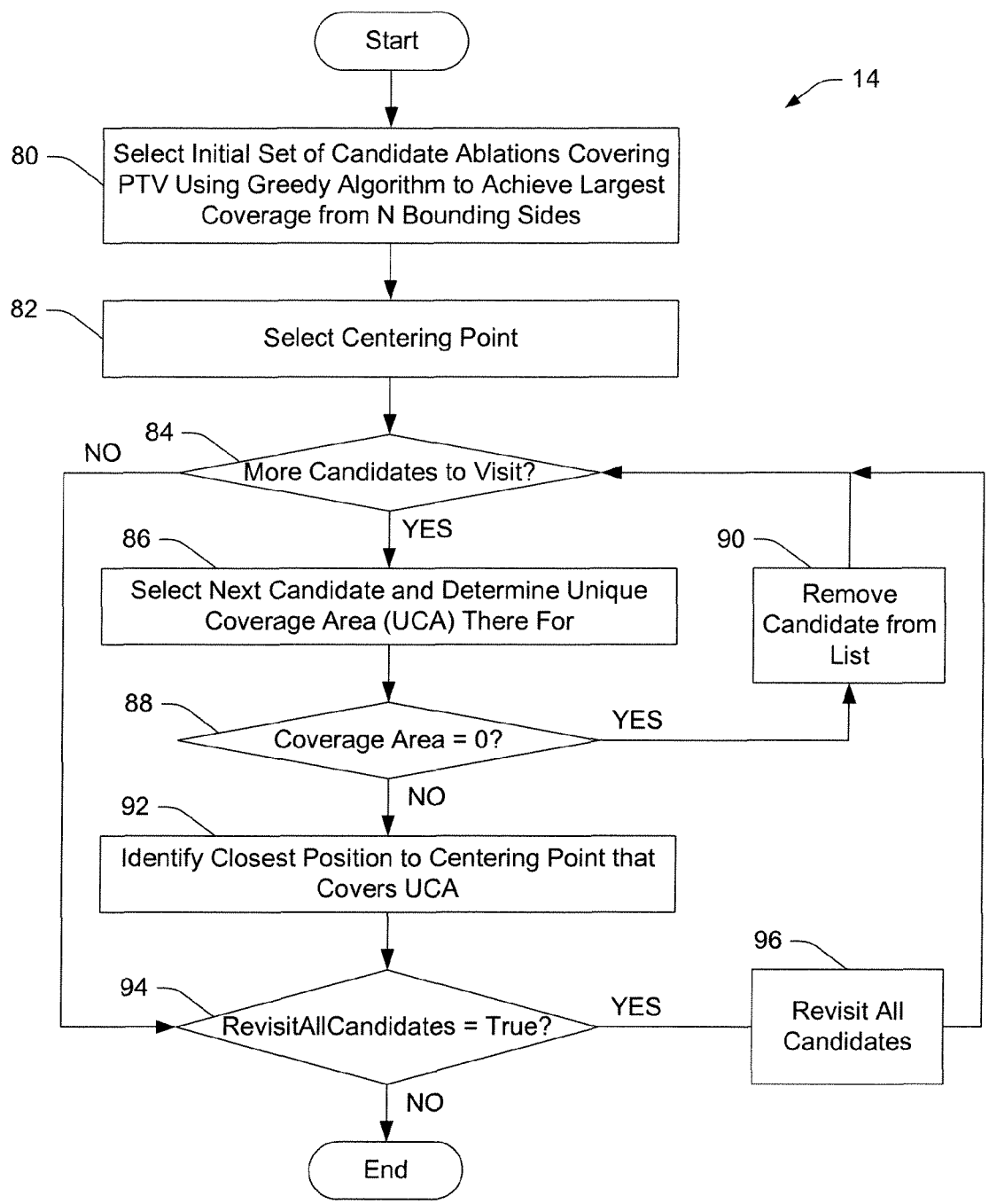

FIG. 5 illustrates a methodology that is performed by optimization component for generating an ablation planning solution, as discussed herein with regard to preceding figures and in accordance with various features.

Figure 6B:
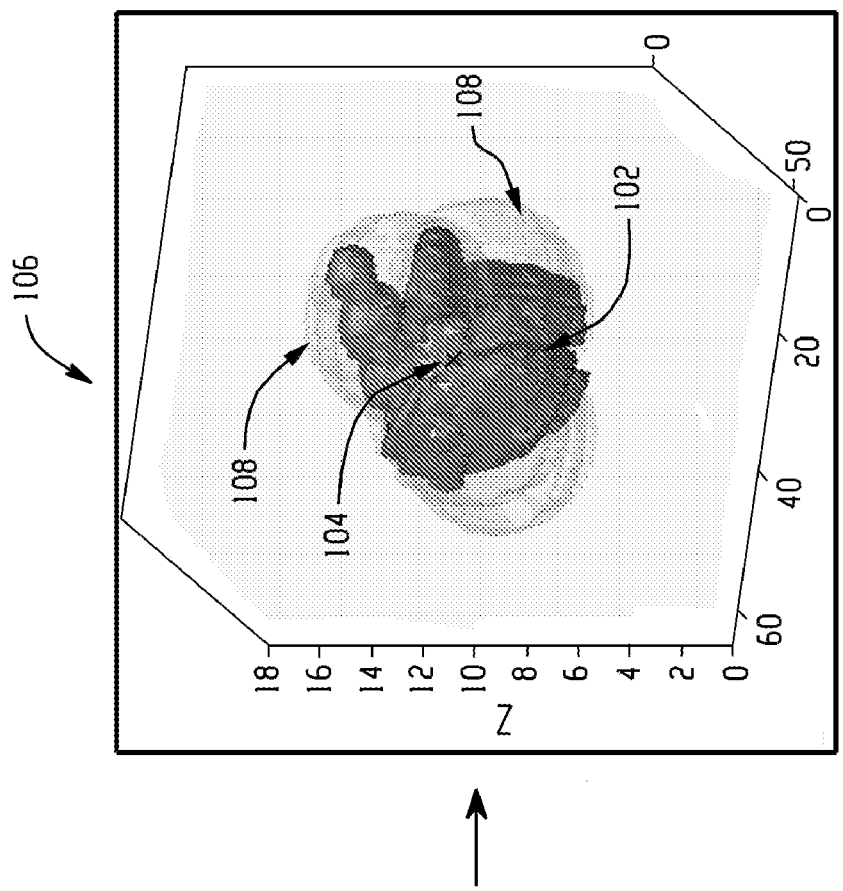
Figure 6A:
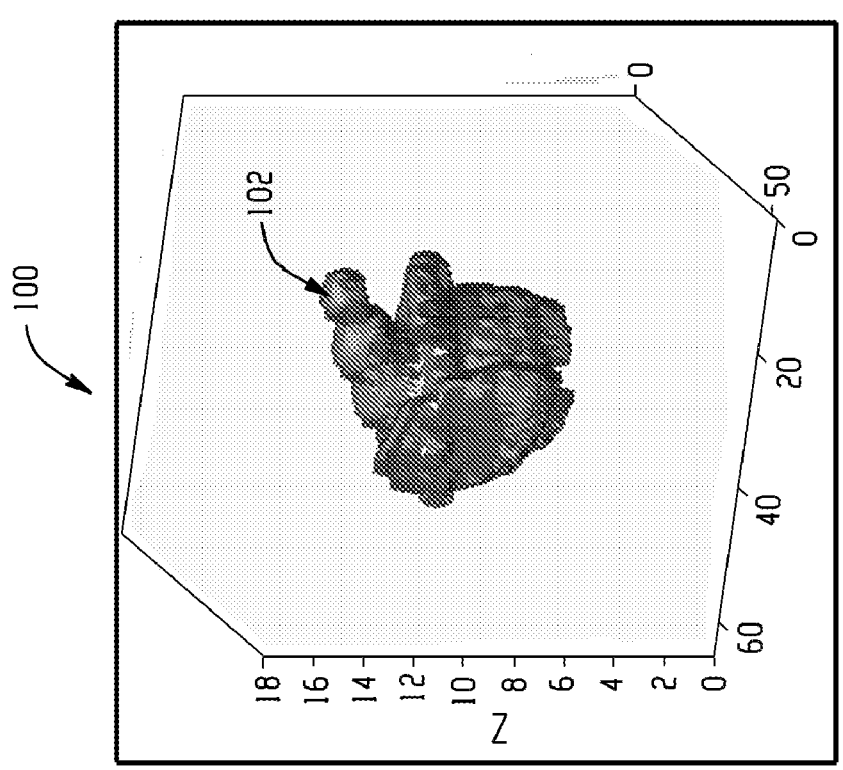

FIGS. 6A-B illustrate a 3D segmented, irregular shape tumor with margin defining a PTV, and a plurality of ellipsoid ablation regions that are computed for a given ablation probe, respectively FIG. 7 is an image of a plurality of ellipsoid ablation volumes, each ellipsoid having a center, which is determined as described herein, and having a known volume that is a function of the selected probe size and ablation duration.

FIG. 8 illustrates an ablation pattern for an ablation probe is depicted by the elliptical region.

FIGS. 9A-B illustrate computer-modeled images of a PTV and candidate ellipsoid ablation volumes that overlap a critical region, such as a bone.

Figure 10:
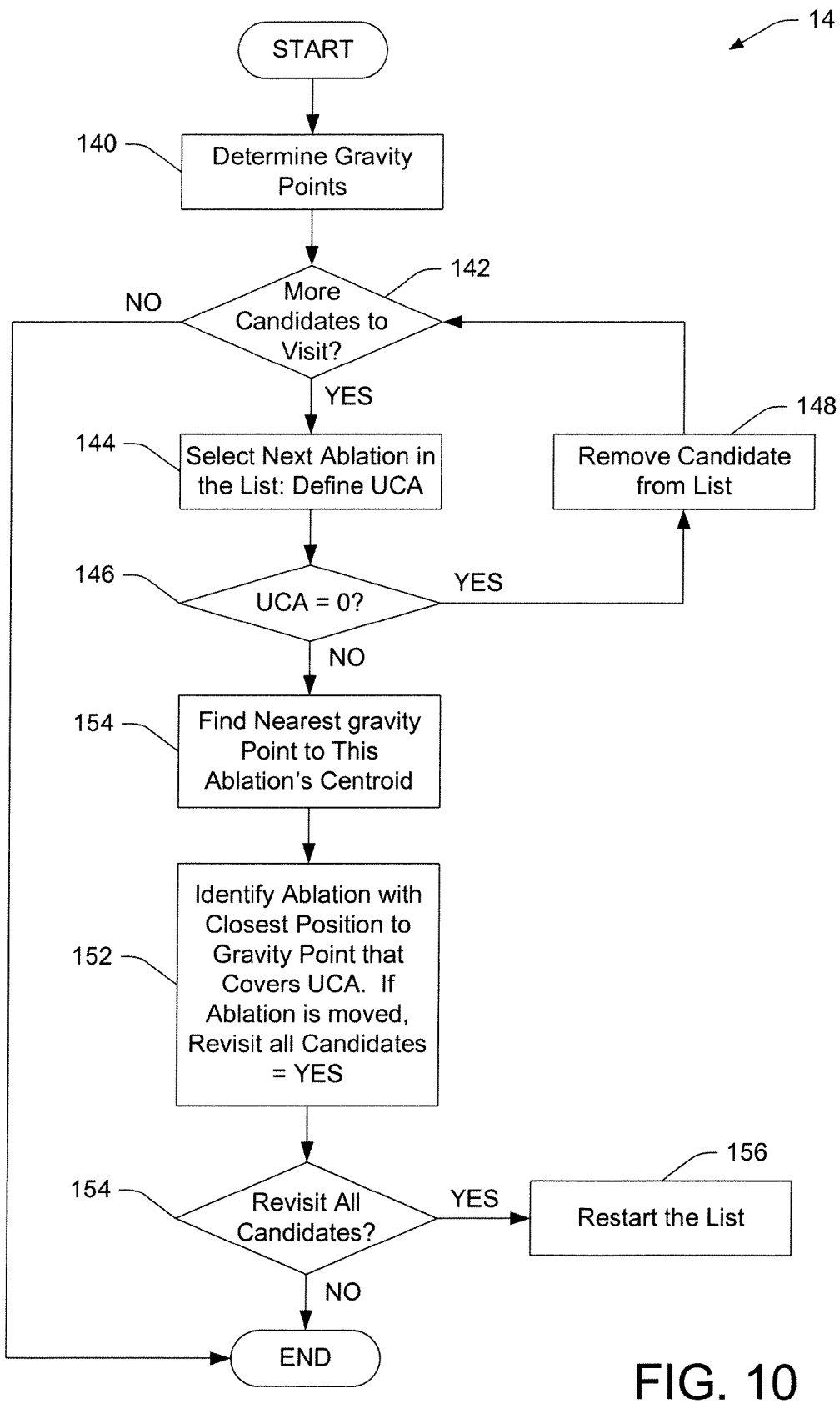

FIG. 10 illustrates a method that is performed by optimization component for planning an ablation procedure, in accordance with some embodiments.

Figure 11:
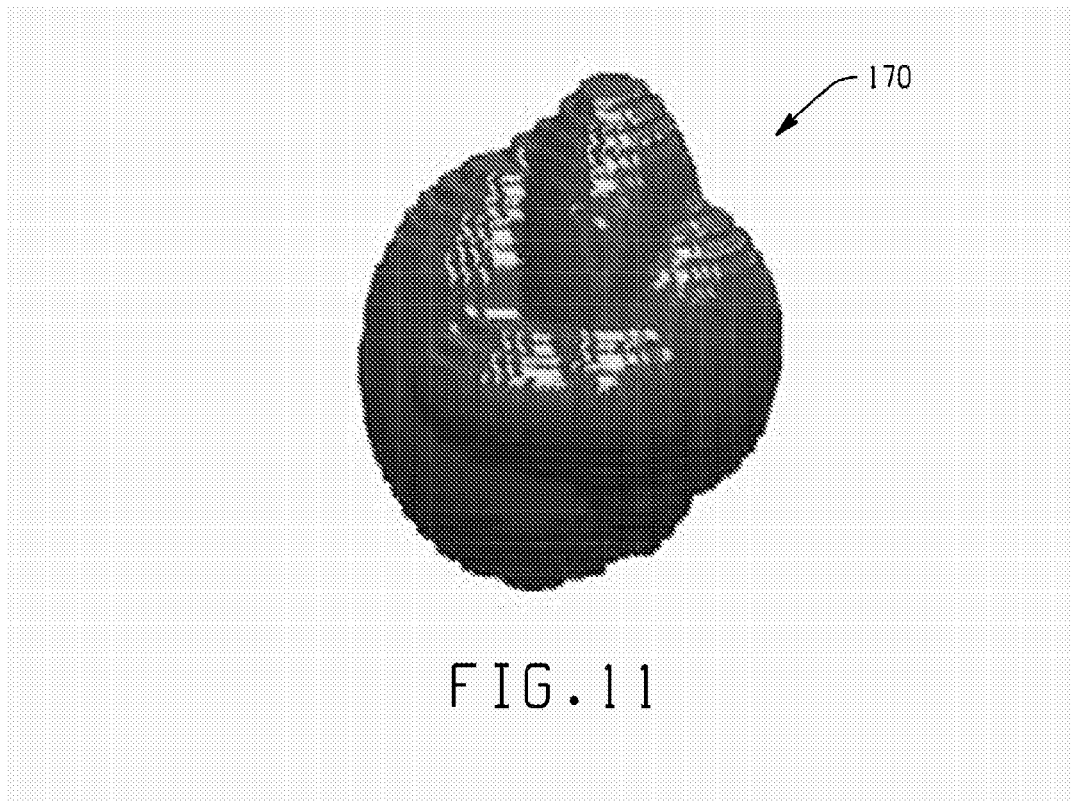

FIG. 11 illustrates an abnormally-shaped PTV that is to be covered by an ellipsoid ablation, such as may be utilized as the ellipsoid ablation volumes in the techniques of the preceding figures.

Figure 12:
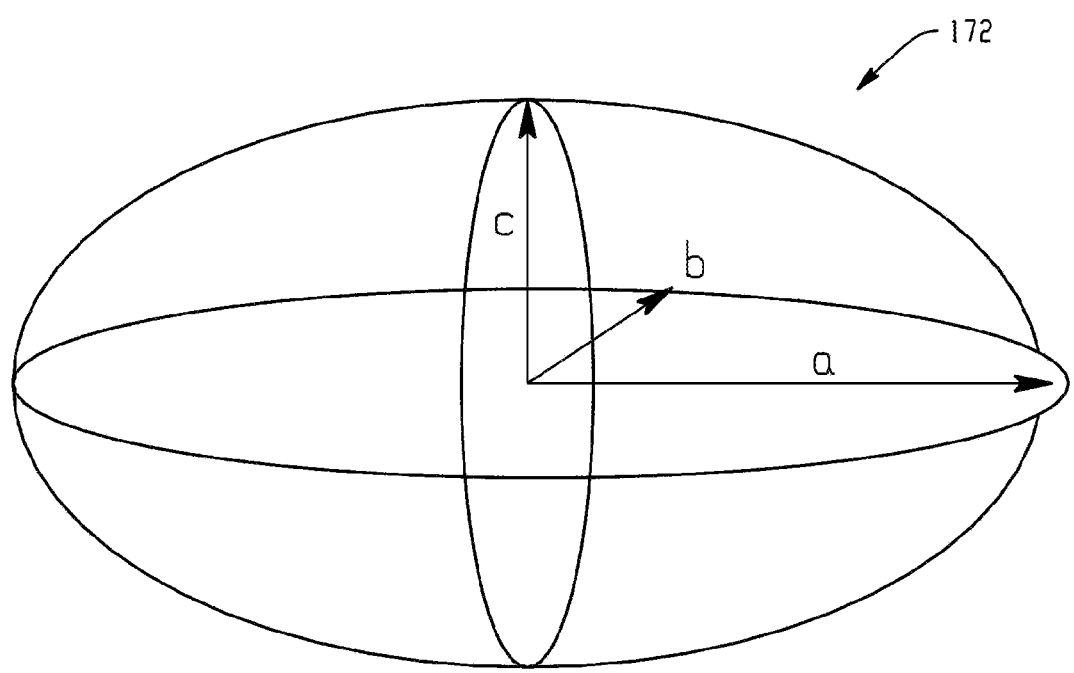

FIG. 12 illustrates the ellipsoid ablation used to cover the abnormally-shaped PTV.

Figure 13:
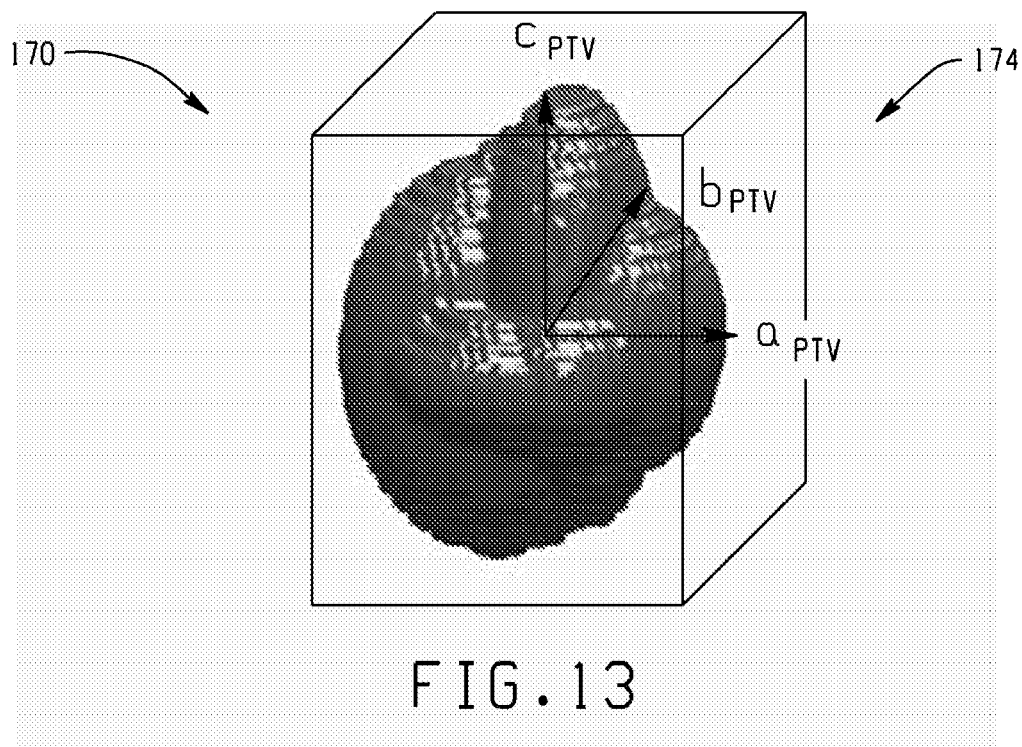

FIG. 13 illustrates the abnormally-shaped PTV after circumscription by a scaled ablation, which can be performed quickly.

Figure 14:
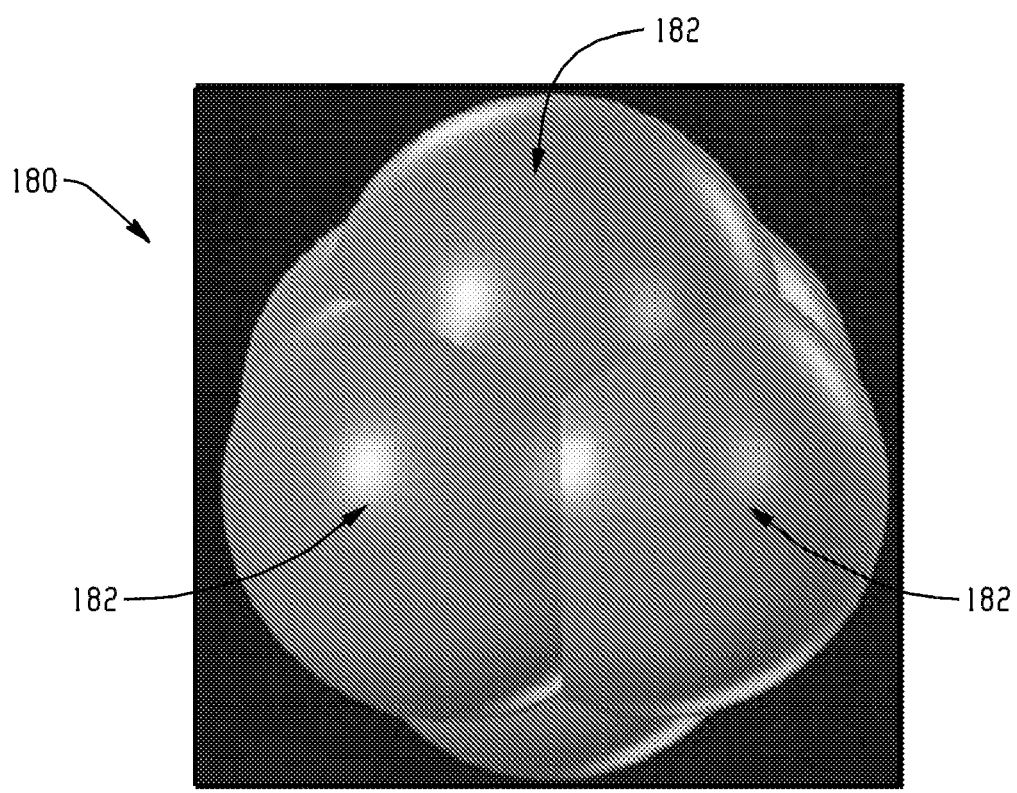

FIG. 14 illustrates a 6-ablation solution selected to cover the sphere for values between 1 and 1.25.

Figure 15:
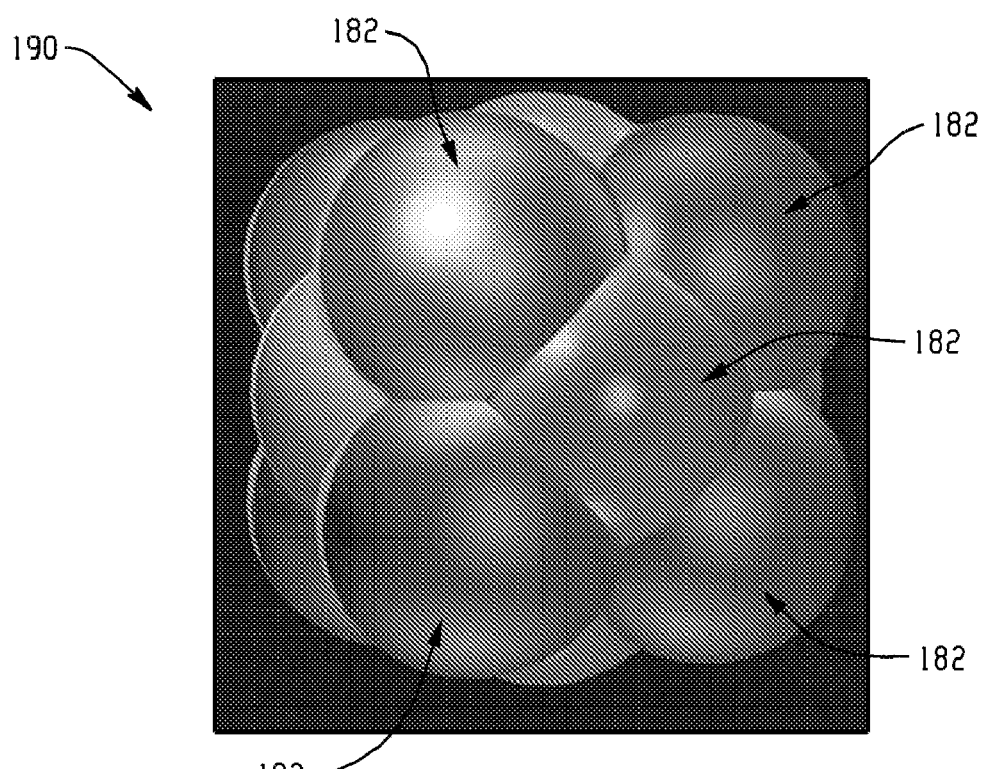

FIG. 15 illustrates a 14-ablation solution selected to cover the sphere for values between 1.25 and 1.66.

Figure 16:
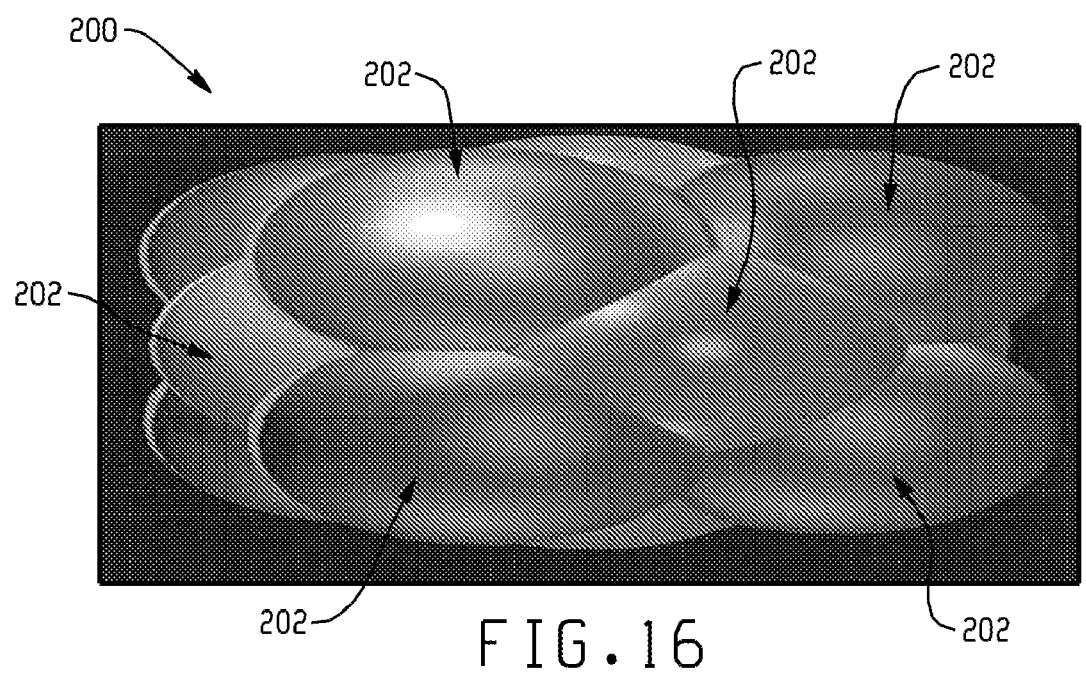

FIG. 16 illustrates a 14-ablation solution after application of the predetermined factor to the ablation spheres.

Figure 17:
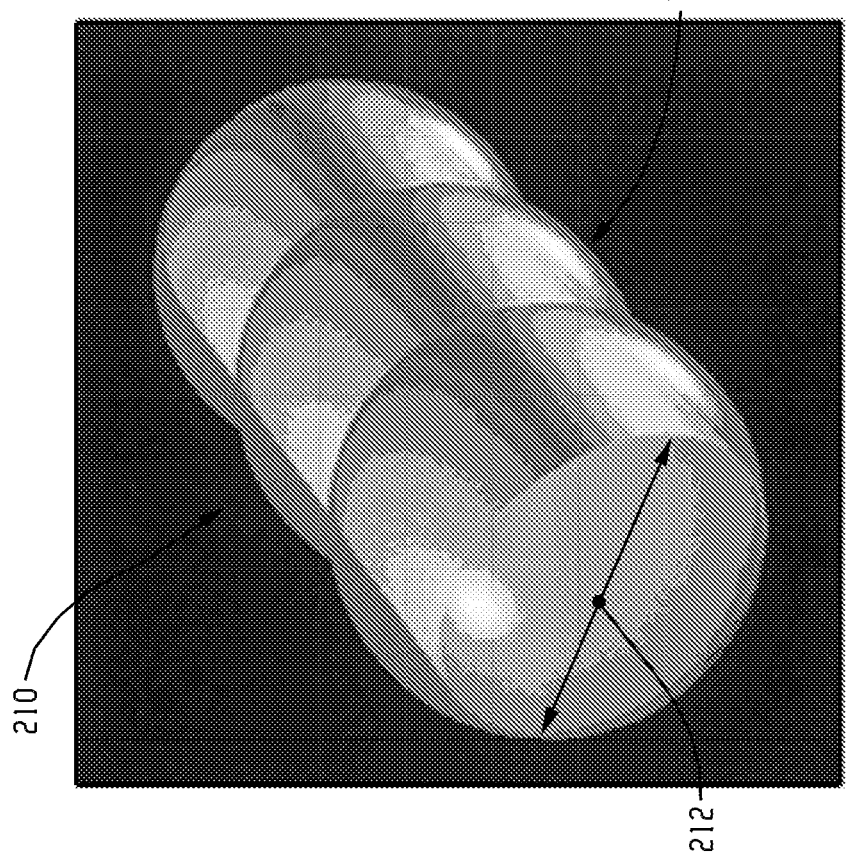

FIG. 17 illustrates an example of a pull-back simple building block (SBB) consisting of 3 spherical ablations.

Figure 18:
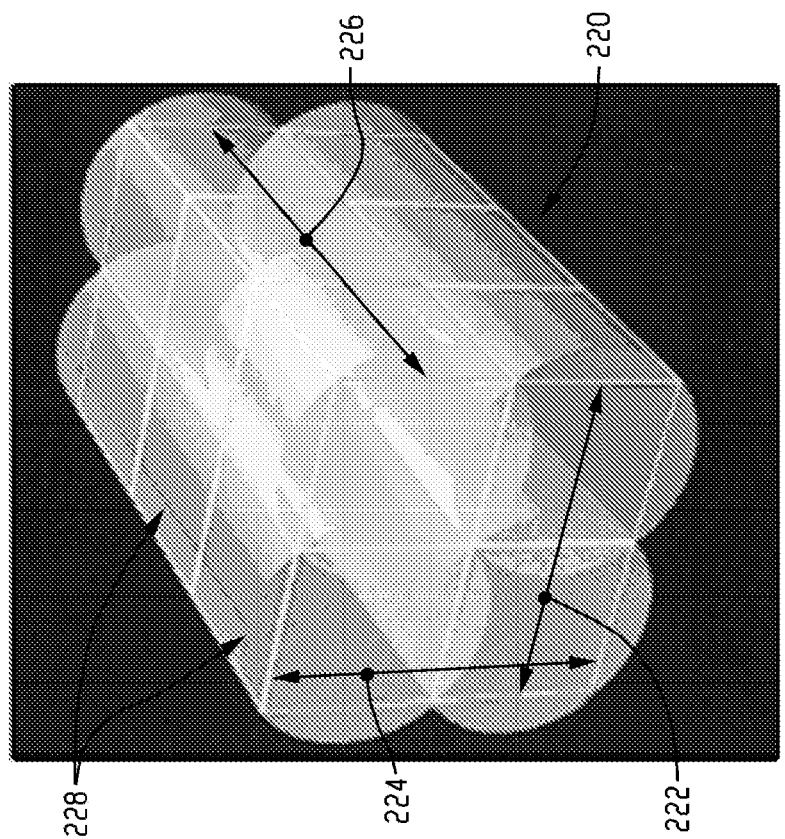

FIG. 18 shows how four SBBs can be used to build a total building block (TBB) to cover a PTV consisting of 2×2×3 cubes.

Figure 19:
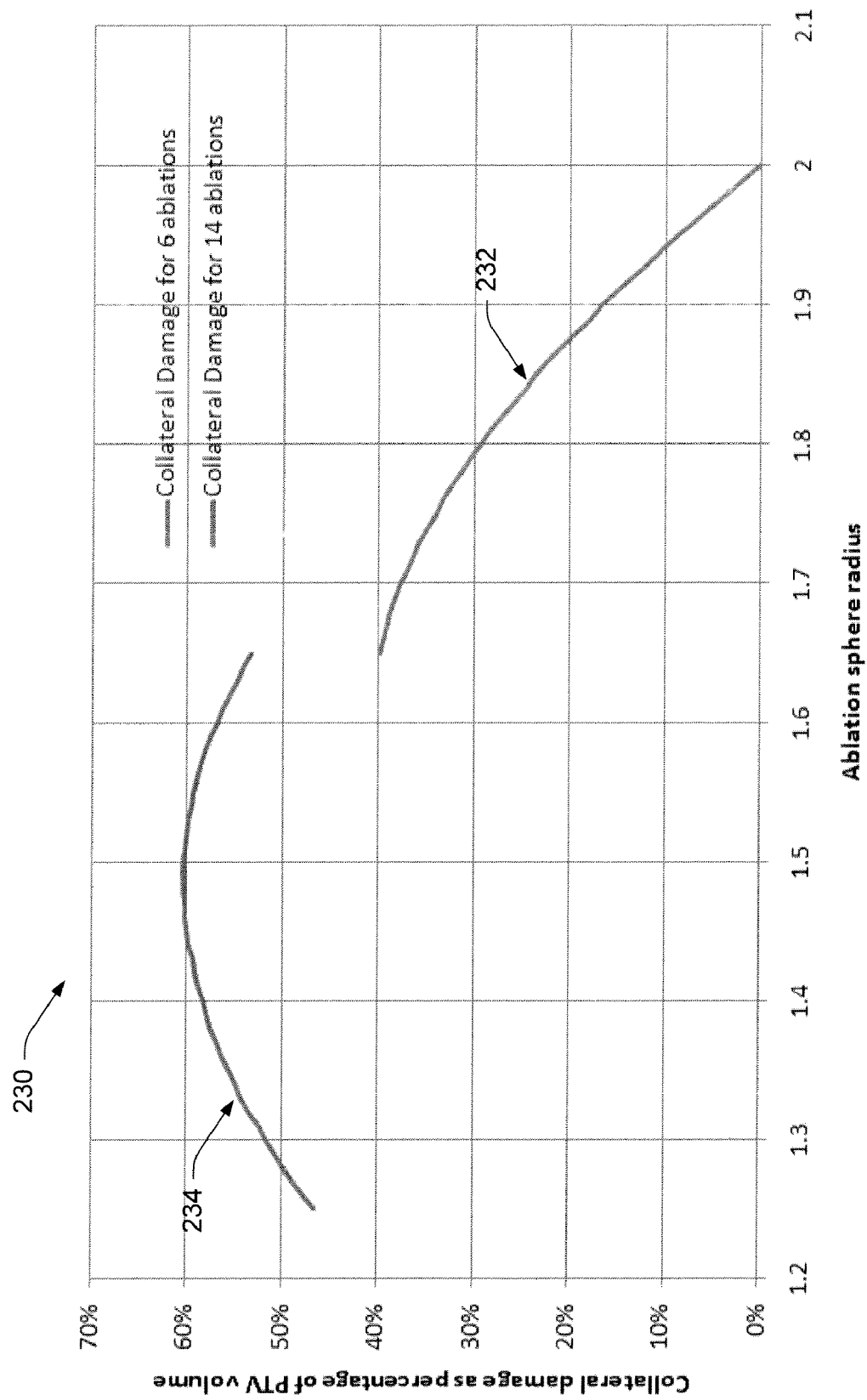

FIG. 19 is a graph with two curves that show that collateral damage is significantly smaller than what would be obtained if the axial or diagonal distances were not adjusted with a reduced ablation radius, such as may be achieved using the CD minimization component.

Figure 20:
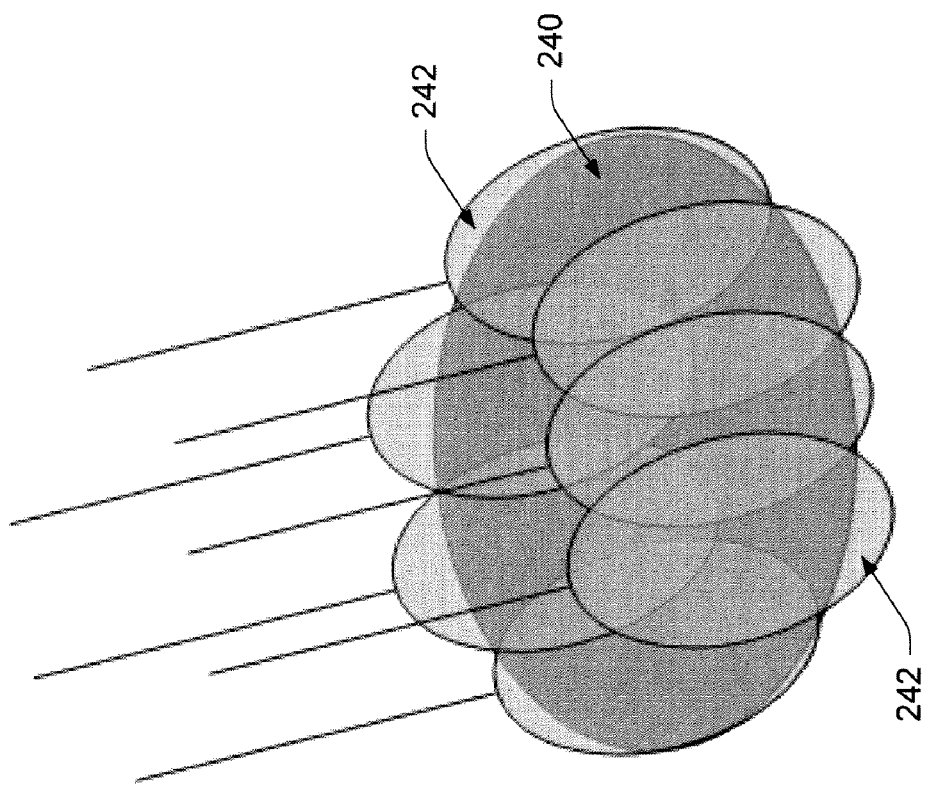

FIG. 20 shows a PTV being covered by multiple ellipsoidal ablations with identical orientation.

Figure 21:
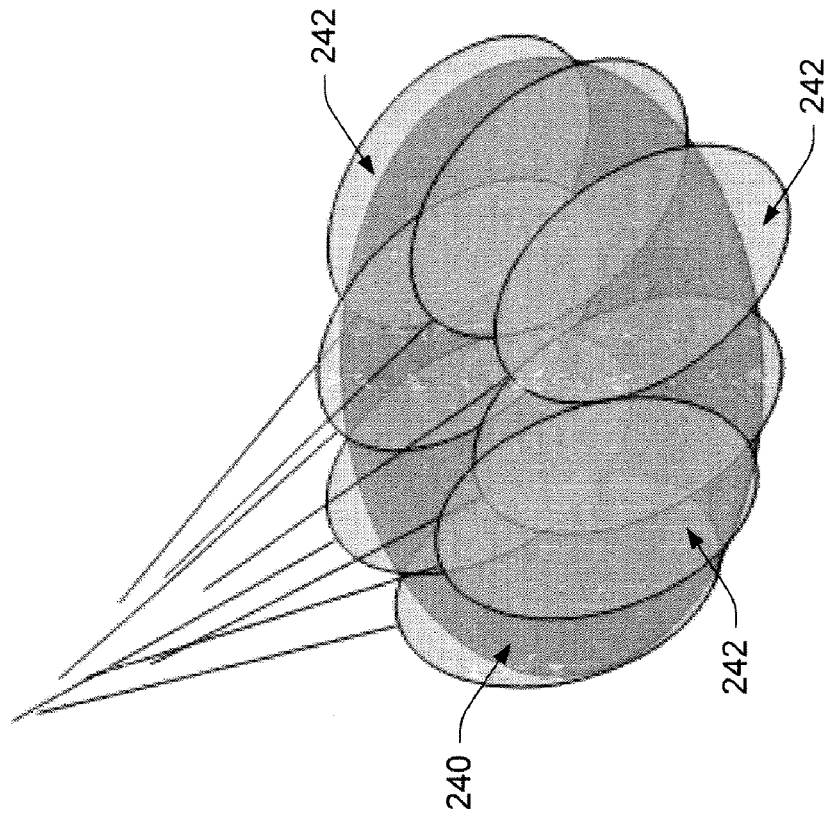

FIG. 21 shows the same PTV being covered by multiple ellipsoidal ablations with variable orientations determined by a fixed fulcrum point that lies on the patient's skin surface.

Figure 22:
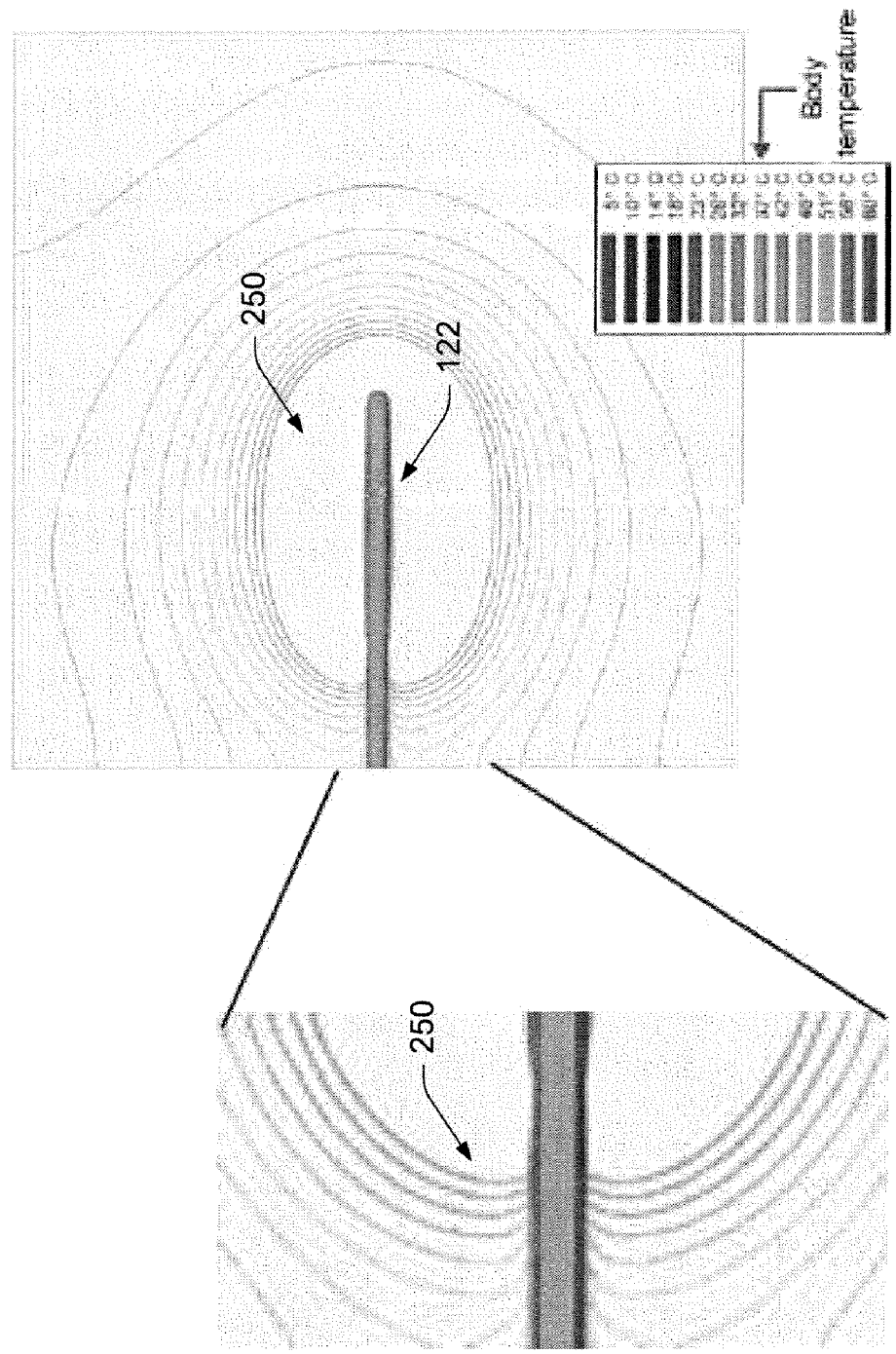

FIG. 22 illustrates an example of an irregular ablation, such as may occur when using a conventional ablation probe tip.

Figure 24:
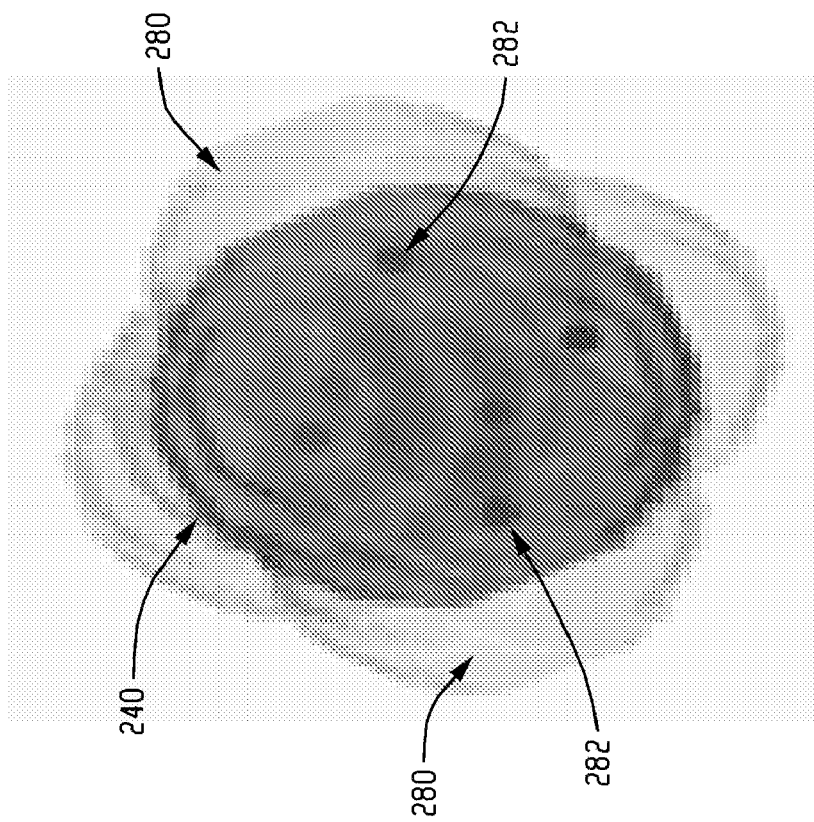
Figure 23:
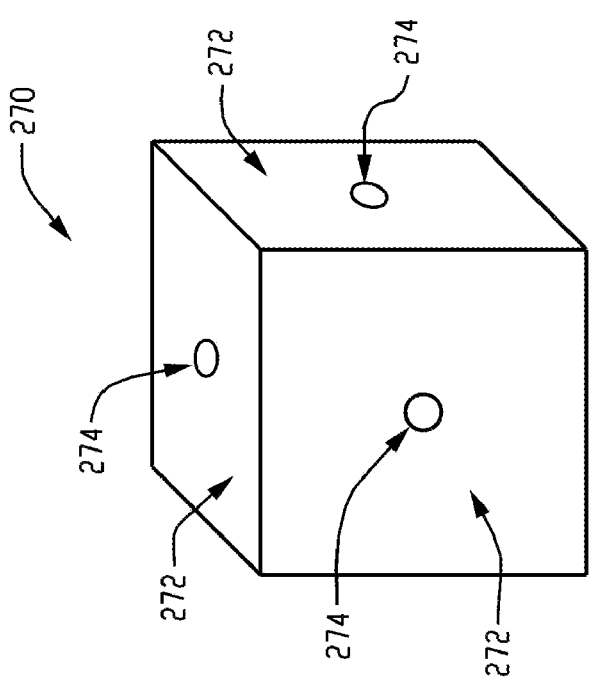

FIGS. 23 and 24 illustrate a bounding polyhedron and a PTV, respectively.

Ablation devices, such as an elongated slender probe, are typically inserted into a tumor, lesion, or other tissue to be ablated, and the probe tip is heated using a radiofrequency energy in order to heat the surrounding tissue to a temperature sufficient to kill cells therein, often considered as 50 degrees Celsius. Although the present application primarily describes radio frequency (RF) ablation techniques, which can be used in many locations, including liver, kidney, breast, lung and others, it will be understood that cryoablation, microwave, and other ablation and treatment procedures can be planned similarly.

An ablation zone is typically located relative to the probe tip and is spheroid or ellipsoid in shape, noting that a sphere is an ellipsoid with equal a,b,c axes. When a tumor is larger than the ablation region for a given probe size, a physician selects more than one probe position to generate a plurality of ablated regions that overlap to cover the entire tumor mass. A typical ablation process involves defining the target region, inserting the probe to the desired location, and applying power to the probe for about 15 minutes, causing the probe tip to heat.

A planned target volume (PTV) is defined that envelopes the entire tumor mass as well as a buffer region (e.g., typically one centimeter or so) around the tumor. This ensures ablation of all tumor cells and microscopic tumor cells, found in the buffer zone, in order to mitigate a recurrence of the tumor.

In accordance with various features presented herein, probe position is selected by determining potential trajectories along which the tumor mass is reached by a probe without passing through critical regions or bone tissue. One or more trajectories are then selected by a physician or automatically to optimize a number of ablations performed to ablate the entire tumor mass.

The described systems and methods, according to one embodiment but not limited thereto, compute precise locations for ellipsoidal RF ablations by scaling ellipsoidal ablation regions to spherical ablation regions. Accordingly, the described innovation(s) take advantage of ellipsoidal ablation region generation techniques such as are described in PCT Application Number WO20081B50087, entitled "RF Ablation Planner," filed on Jan. 10, 2008, which is hereby incorporated by reference in its entirety. These techniques are described below with regard to FIGS. 1-10.

Figure 1:
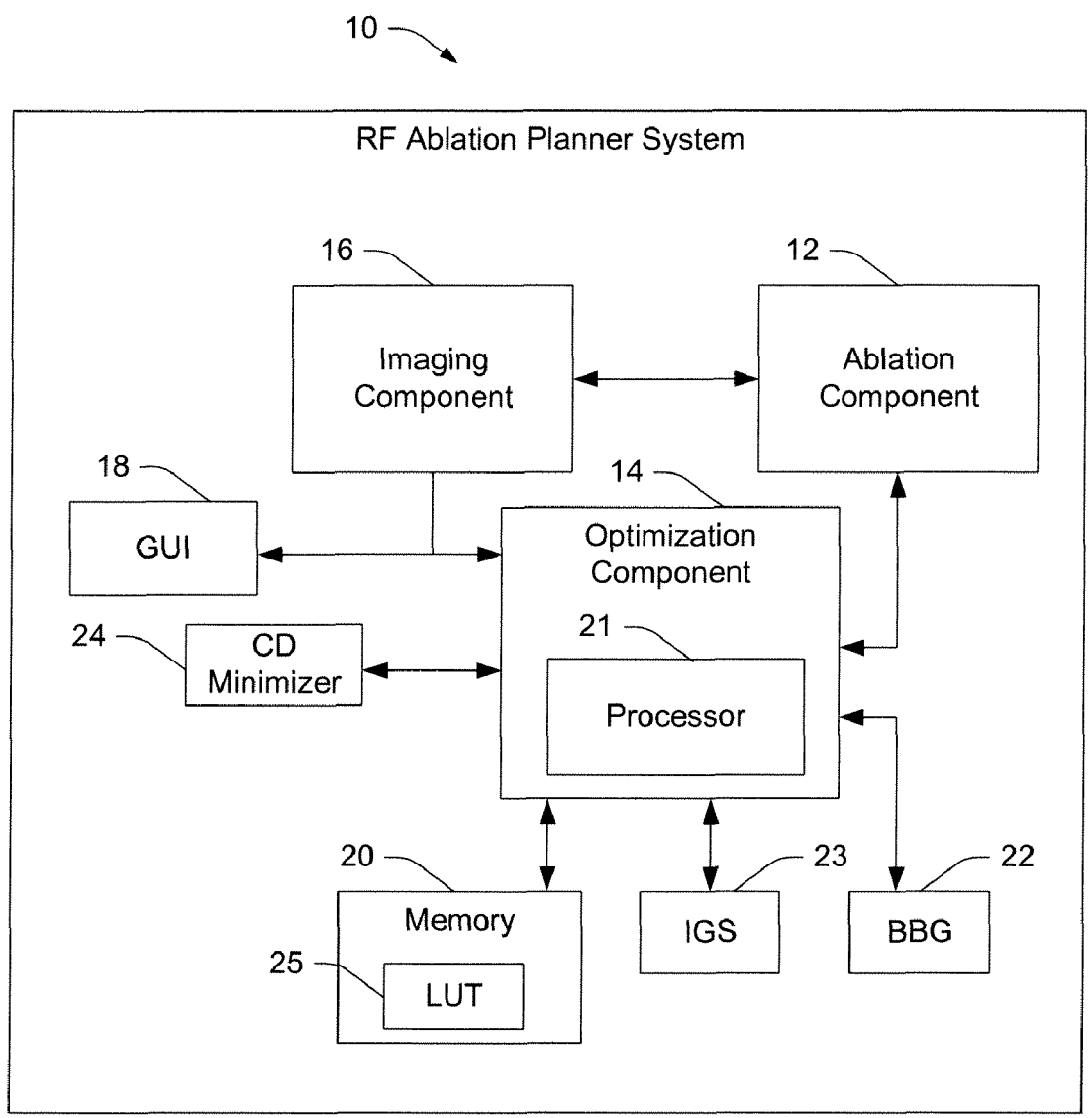
FIG. 1 illustrates a radio frequency (RF) ablation system that facilitates generating a plan for performing one or more ablation protocols to treat a tumor mass or lesion in a patient.

FIG. 1 illustrates a radio frequency (RF) ablation system 10 that facilitates generating a plan for performing one or more ablation protocols to treat a tumor mass or lesion in a patient. Successful treatment of large tumors can be achieved by planning ablation probe positions precisely so that no part of the tumor is left untreated and accurately executing the plan. The system 10 generates a quantitative ablation plan, including target positions and orientations for each ablation. It may optionally identify the entry point or points on the outside of the body that lead to the target(s). The ablation plan ensures that all areas of the tumor are covered, and reports the number of ablations required for complete ablation using a particular probe. The system 10 also utilizes optimization techniques to minimize the number of ablations. Since the plan is quantitative, it can be carried out using a robot and/or by using registered image guidance, such as by quantitatively tracking the ablation probe.

The system 10 includes an ablation component 12 that is operatively connected to each of an optimization component 14 and an imaging component 16, such as a CT scanner. The system 10 can additionally or alternatively include an ultrasound imaging component, an X-ray fluoroscopy imaging component, a magnetic resonance imaging system, a picture archiving and communication systems (PACS) or any other suitable imaging component or delivery system. The ablation component 12 in one embodiment is an RF ablation system, which includes a power source, a radio frequency generator, a probe operatively coupled thereto, etc., as well as any other suitable component to facilitate inserting the probe into a tumor mass and heating the tumor mass to a temperature sufficient to kill tumor cells (e.g., approximately 50 degrees Celsius) within a region relative to the probe tip. The ablation component 12 in an alternative embodiment includes a high-intensity focused ultrasound component (HIFU), which ablates tissue in a particular region through the use of mechanical vibration and/or heating properties of ultrasound. In some systems, an ultrasound ablation region can be predicted, even if the ultrasound is not strictly 'focused', using an array of transducer elements. The imaging component 16 generates data which is reconstructed into a 3-D image. Objects such as a lesion, organs, critical regions can be segmented automatically using algorithms or by hand with drawing tools along each of the axes. The segmentation produces a description of the volumetric regions associated with the specific objects. In particular, a volume may be optionally presented to a user via a graphical user interface 18 (GUI). The volume may be 'grown' by a desired distance so that the tumor plus margin are included in the resulting volume. Whenever the word 'tumor' is used herein, particularly regarding optimization, it is assumed to mean the 'Planned Target Volume' (PTV), which covers the specified tumor plus margin that together are intended for full coverage. Medical image viewing and image processing systems provide capabilities to either manually or semi-automatically segment objects from medical images. Some systems also enable the user to set a margin around a segmented tumor to define a new volume, the PTV. The optimization component 14 analyzes information associated with the PTV, particularly the dimensions, and for a given ablation probe defines a set of ablation positions with orientations. In one example, the optimization component 14 identifies the fewest number of ablations possible that cover the PTV. In another example, the optimization component 14 identifies the ablation positions with orientations that spares the most healthy tissue (i.e. minimizes collateral damage). In another example, additional object volumes are segmented that denote 'critical regions' of tissue or bone that are not to be ablated, and the optimization component 14 attempts to generate either the fewest ablations or minimize collateral damage, while also avoiding these regions. In some cases however, the optimization component 14 produces unablated areas, whereupon the user is alerted and the regions can be displayed on the User Interface. Information associated with ablation techniques, ablation periods, probe size, temperature, PTV, ellipsoid volume, ellipsoid centers, PTV reductions and/or adjustments, protocols for minimizing PTV, probe entry angles and/or positions, and any other suitable information related to system performance is stored in a memory 20, which is also operatively coupled to the optimization component 14. Additionally, optimization component 14 includes a processor 21 for performing various analytical actions, executing one or more routines, and the like. For example, the processor 21 can and can execute routines such as those described with regard to FIGS. 2, 5, and 10. According to some aspects, the optimization component comprises a computer that includes one or more processors and memory that stores information related to ablation techniques.

The probe entry angles may be selected by the doctor and entered manually or graphically via the user interface. Alternatively, the system 10 can facilitate the selection of probe entry angles that avoid "critical regions," as the probe travels through the body to the tumor. In theory, critical regions that should be protected from ablation may be different from other critical regions that can be punctured by the probe entry path. In RF ablation, the current probes require a physical path between the skin and target. In other ablation techniques however, such as HIFU, the target may be reached without disturbing the intervening tissue. However in practice, critical regions for ablation and entry path are often the same. The optimization component 14 selects ablation volumes that do not intersect a critical region. In some cases, a critical region may be so close to the tumor that it cannot be easily accessed. In this situation, the critical region is highlighted to alert a user that additional preparation procedures are desirable or recommended, such as injection of saline to separate or thermally insulate the tumor from the critical region.

The selection of probe entry points (optional) and ablation points (e.g., placement of the probe tip with a given offset for the expected ablation shape) is performed by the optimization component 14. According to other aspects, the optimization component 14 provides a plurality of suggested entry points and/or ablation points, which are presented to a user via GUI 18 for selection. In this manner, the RF ablation planner system 10 facilitates successful treatment of large tumors through planning the ablation positions precisely so that no part of the tumor is left untreated, no critical tissue is damaged, the plan generates quantitative goals enabling the ablation component 12 to use tracking or control to improve accuracy, and an overall system with more repeatable procedures.

According to other embodiments, a PTV for a tumor mass is pre-generated and stored, and is imported to the optimization component 14 at a later time for ablation procedure planning. The imported PTV is a three-dimensional representation of the PTV, which is generated using the imaging component 16, such as a CT scanner, an ultrasound imaging component, an X-ray fluoroscopy imaging component, a magnetic resonance imaging system, a picture archiving and communication systems (PACS) or any other suitable imaging component or delivery system. Once the PTV has been received, ablation volume centers are identified for one or more ablation volumes that completely envelop the PTV. The target ablation points (e.g., the centers) can be output to a tracking system, which may include a GUI, to assist a physician in probe placement along an intended insertion trajectory. Additionally or alternatively, the target ablation points may be output to the GUI 18 (e.g., with or without the tracking system) for approval and/or use by a physician when performing the ablation procedure.

In another embodiment, the ellipsoid ablations are generated by first generating spheroid ablations and stretching or compressing at least one axis thereof (e.g., multiplying the axis by a predetermined factor), as described below with regard to FIGS. 11-16. For instance, a plurality of precomputed geometrical solutions comprising N ablation spheres, where N is an integer greater than 1, are generated to cover a PTV and stored to the memory 20 (e.g., a lookup table 25 therein). When planning an ablation procedure, the PTV is enclosed in a sphere by the optimization component 14, which then accesses the lookup table to identify a pre-computed solution to cover the PTV sphere. The pre-computed solutions can be scaled up or down to cover the PTV while minimizing collateral damage to surrounding tissue.

In another embodiment, the ablation planner system 10 includes an ablation building block generator (BBG) 22, which may be manual or automated, and which uses as input the type of ablation device to be used and/or the geometric description of the individual ablation shape generated by the device. Optionally, the BBG takes as input one of a selection of building block "types," such as "axial pull-back," "lateral side-by-side," etc., describing the nature of the geometric relationship between individual ablations in a building block. Additionally, the BBG may receive as input building block parameters, such as the number or spacing of individual ablations in a building block. Instead of the optional input arguments, the BBG can suggest optimal block types and parameters based on the individual ablation shape and the PTV size and shape. The foregoing inputs may be entered by an operator into the system 10.

The BBG creates as output the geometric description of one or several building blocks, which can be used by the planning system to create optimal coverage of the PTV.

Optionally, an image guidance system (IGS) 23 is included that can import the building-block-based treatment plan, and which can (a) guide the physician to place the ablation device in each building block location, (b) at each building block location, give specific feedback on how to create the building block (e.g. Indicate "Pull back 15 mm," and display the actual pull-back distance in real time, e.g. using a spatial tracking system).

In one embodiment, the coverage planning is based not on individual ablations, but on easy-to-create "building blocks" consisting of multiple ablations. This is achieved by providing a software module and graphical user interface (GUI) that serves as the building-block generator, which executes the following workflow. First, a 3D medical image (CT, MRI, PET, . . . ) of the area of interest in the patient is obtained. The PTV is then segmented, and the BBG 22 generates the optimal building block(s) for the ablation procedure. The ablation planning system 10 creates a composite ablation plan based on the generated building block(s), i.e. the positions and orientations of individual blocks that are necessary to fully cover the PTV with the smallest number of blocks and/or time. The plan is transferred to the image guidance system 23 (or navigation system), where the individual building block locations are highlighted as "targets," and the guidance system facilitates sequential delivery of the ablation device to each target. Also, at each target/building block location, the system gives specific guidance as to how to create the building block in an optimal fashion (e.g. displays the requested and actual amount of pull-back along the needle axis).

An ablation is performed after medical imaging and/or the navigation system has confirmed correct placement of the device. Ablations are repeated until the ablation plan is fully executed, i.e. until the PTV is fully covered with ablations. Optionally, if ablations were performed at locations other than those in the plan, or if medical imaging or other feedback indicates that the ablation size or shape differs from that assumed in the plan, the ablation plan can be updated by subtracting already performed ablations from the PTV, and creating an iterative/updated plan for the remainder of the PTV.

The BBG subsystem 22 includes a software module and GUI that enables manual or automated definition of the ablation building blocks. Two types of building blocks can be generated for planning: "total" and "simplified" building blocks. The Total Building Block (TBB) is the union of all individual ablations in the building block. The Simplified Building Block (SBB) is the largest "simple" geometric shape (such as a sphere, ellipsoid, cylinder, cube . . . ) that can be fully inscribed in the TBB. Depending on the computational complexity of the specific planning problem, either the TBB or SBB may be used for planning. For manual planning in particular, the SBB is advantageous.

The most commonly used building block is the "pull-back" building block, which consists of 2 or more individual ablations performed by pulling the ablation device back toward the skin entry after each ablation. Examples of pull-back building blocks are discussed with regard to FIGS. 17 and 18, below.

In another embodiment, the ablation planning system 10 includes a collateral damage (CD) minimizer 24 that reduces collateral damage to tissue surrounding the PTV. The CD minimizer is described in greater detail with regard to FIG. 19.

In another embodiment, the entry point of an ablation probe is used as a fulcrum by which the ablation probe tip is moved to different ablation locations to cover the PTV, as described in greater detail with regard to FIGS. 20 and 21.

In yet another embodiment, a user executes a pilot or test ablation using the ablation component 12, and the imaging component 16 images the pilot ablation and stores the image data to the memory 20 (e.g., via the processor 21). The processor 21 uses the actual ablation volume determined from the pilot ablation in place of the ellipsoidal ablation volume(s) to plan an ablation procedure. In this manner, imperfections in ablation shape can be accounted for before performing the ablation procedure, to ensure complete PTV coverage and ablation success. This aspect is further discussed with regard to FIG. 22, below.

Figure 2:
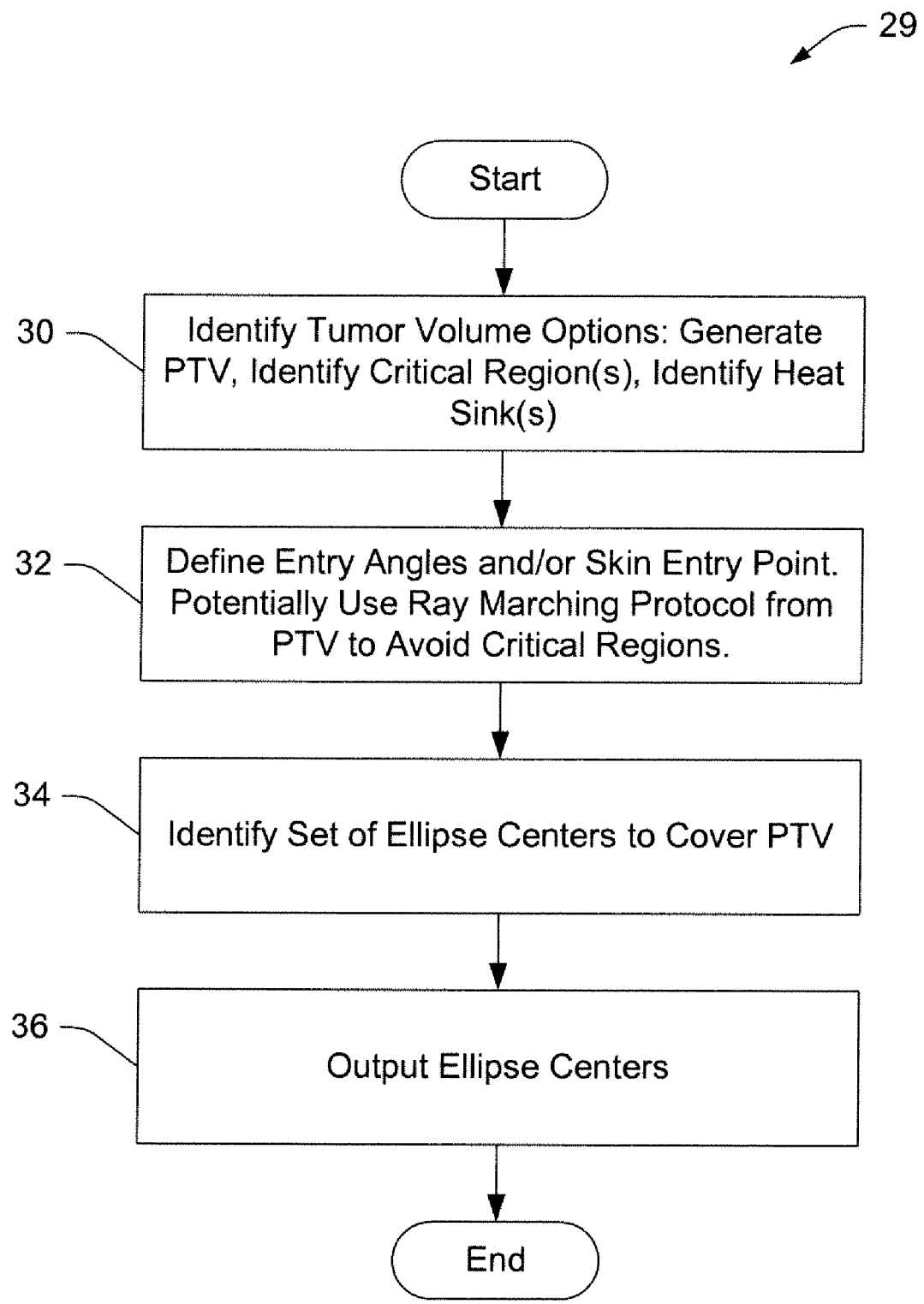
FIG. 2 illustrates an algorithmic method that generates a quantitative plan, including entry angles for an ablation probe and a target position for each ablation.

FIG. 2 illustrates an algorithmic method 29 that generates a quantitative plan, including entry angles for an ablation probe and a target position for each ablation. The algorithm assures all tumor areas are covered and determines the ablations for complete tumor ablation using a particular probe. Additionally, the algorithm includes optimization techniques that minimize the number of ablations for a given tumor volume. In one example, the algorithm identifies a plurality of ablation ellipses that cover a planned target volume (PTV). The centers of the ellipses are pulled toward a centering "gravity point," which is located at the center of mass. Typically this falls within the PTV, however some unusual shapes, for example a 'C' shape, the point may actually be outside the PTV. As ellipses are pulled toward the gravity point, those ablation ellipsoids that do not cover a unique portion of the PTV are deleted to identify a minimal number of ablation ellipsoids and their respective centers. This occurs when enough ellipses are clustered so that an ellipse's critical coverage area is already covered by other ellipses. Once the ellipses are pulled together, the collateral damage is minimized.

According to the method, at 30, a tumor volume is segmented and identified. The tumor can be any shape, and can be a collection of disconnected region. The PTV is then identified for ablation, e.g. the tumor volume plus an approximately centimeter-thick surrounding volume. FIG. 3, below, shows an example tumor that is grown by a fixed size in all dimensions. Although a circle is shown for this 2D example, a sphere can be used in the 3D example. Placing the center along the edge of the tumor forms a PTV boundary. This can be performed by other techniques as well. The best results can be obtained if disconnected regions are close together, ideally connected by the margin. If they are not connected, then it may be preferable to consider each cluster of margin-connected volumes as separate tumors for planning purposes. The PTV represents a volume with added margin around the tumor. Critical regions and heat sinks near the tumor are additionally identified at 30, typically by any of numerous segmentation techniques described in the literature and available in products. Each critical region, heat-sink, tumor, PTV, etc. is a region of interest (ROI). The machine segmentation can be automated, performed by manual outlining or a combination of both. Critical regions are organs or life-critical tissues that can be adversely affected by the heat. There are actually two types of critical regions. The first are those near the PTV, which should not be ablated. The second are those that are not to be punctured such as when an RF ablation probe enters the body. The bowel is a structure that should not be punctured or ablated. The primary affect is on workflow however. A physician may compute a set of ablations and then go to the extra work of segmenting only relevant (near PTV or near insertion path) critical structures to determine how they change the proposed procedure. For example, nerves that are near the proposed ablation area may be added afterward to see how the plan would have to change, and whether the procedure seriously risks those nerves. Other structures are segmented and identified as "heat sinks." For example, although it may seem that a critical structure such as the aorta should be protected from ablation, it actually protects itself because the blood flow is so rapid that it "self cools." The cooling causes problems however to nearby structures that require ablation, since the cooling competes with the heating process, resulting in an unablated area and risk of cancer relapse. In current RF ablation probes, the temperature after 15 minutes is higher near the probe than at the edges of the ablation region. Therefore it may be advisable to move the probe 3 mm closer to the aorta, so that the temperature near the surface of the aorta is closer to 55 degrees C. Computational fluid dynamics, based on the Navier-Stokes equations that describe liquid and gas flow, can be used to estimate the amount of heat that is lost due to proximity of a particular heat sink of a particular size and blood velocity.

At 32, entry angles and/or one or more entry points on a patient's skin are defined. In one embodiment, a ray marching protocol is employed to determine an entry point. The CT voxels are labeled as either 'free' or 'critical region', for example in a binary volume. A ray marching algorithm, such as the one introduced by Perlin (see, e.g.: K. Perlin and E. M. Hoffert, "Hypertexture", Computer Graphics, vol. 23, issue 3, pp. 253-261, 1989), is employed to identify locations on the skin that permit insertion of a probe into the PTV along a path that does not travel through a sensitive or critical region such as bones. Intuitively, this is similar to setting a light at the center of the tumor, having the critical regions (e.g., solid masses such as bone or the like) block the light, and identifying points where the light reaches the skin. A ray of light is "marched" from the center of mass (centroid) of the PTV in a linear 'ray' through the 3D image until one of three situations occurs:

1) The ray reaches the edge of the image volume, whereupon it restarts at a new orientation from the center of the PTV 2) The ray reaches the skin or another location approved as an entry point, whereupon the x,y,z location and ray orientation are be noted. This is a potential entry point, which may be shown graphically or stored in a list for selection or may be evaluated to determine the number of ablations required for coverage from this angle.

3) The ray reaches a voxel that is labeled 'critical region', whereupon a new ray is begun with a new orientation from the center of the PTV.

This procedure continues until all desired angles are evaluated. The choice of potential angles can be based on brute force discretization of orientations, random selection, narrowed by conventional protocol, or simply picked by the physician on the GUI. The ray marching procedure is analogous to the idea of placing a tiny light at the location of the PTV centroid, where critical regions block the light from reaching the skin for example. Lighted areas on the skin are therefore potential entry points and shadowed areas are not. The entry angle is important both clinically and computationally. The entry angle should be safe, avoiding critical regions, as described by this step. Clinically, it is preferred in the liver for example, to puncture the liver capsule only once, from one external location, and generate substantially parallel ablations to cover the PTV. This simultaneously reduces the computational complexity of the problem, since the coverage can be computed assuming a fixed orientation. Since ray marching is faster than the coverage analysis, pre-computing a subset of feasible entry points limits the number of coverage calculations.

At 34, a set of ellipse centers is defined, such that a plurality of 3-D ellipsoidal ablation volumes corresponding to respective ellipse centers collectively envelope the entire tumor mass. The ellipses have a geometry defined by standard a,b,c semi-axis values, satisfying $x^2/a+y^2/b+z^2/c=1$, translated to the identified centers and rotated by a given entry angle, such as is defined by 32. For example, a given ablation probe has a known ablation volume X based on it's a,b,c values and orientation. In one embodiment, Y ablations of the known volume X completely cover the PTV. Probe dimensions can be selected by a user (e.g., depending on the type of probe), and the system can optimize probe placement for the assigned or derived orientation. This method for determining ellipse centers also prevents the ablation of critical regions, and is described further in FIG. 5.

At 36, the identified ellipse centers for the given probe size are output to a user, such as a physician or the like, via the graphical user interface such as is illustrated in FIG. 7, to permit the user to evaluate and/or execute the model. In this manner, the method 29 facilitates planning an ablation procedure to perform multiple ablations at different points, which in turn permits ablation of multiple ellipsoid volumes that overlap in space to ensure ablation of a non-uniformly-shaped tumor volume while avoiding regions in which ablation may be detrimental. A physician may also adjust the ellipses for factors not represented in the model. The ellipse centers along with the specified ablation probe geometry and orientation can be communicated to the ablation component 12. The ablation component 12 can then be used in conjunction with a tracking or robotic system. A tracking system provides visual feedback to the physician on the position and orientation of the tool, or tool-tip in real-time. The target can be displayed along with the live tracked location, often along with a registered patient image. Alternatively, a robot can be given the target point and can carry out the maneuver, with feedback from the tracking system and approval to proceed from the physician.

The ablation ellipses are placed so that they completely cover the PTV. The ellipses typically overlap, and may extend beyond the edges of the PTV. Once the routine 28 minimizes the number of ellipses their centers, i.e. the probe tip locations are other identifier of the probe locations is communicated visually to a physician, FIG. 3A shows an example PTV 40, near the aorta 44. In this case, the aorta has a thermal effect that tapers off to the distance shown as 42. The thermal change is the net result of the ability of the RF ablation probe to heat to at least 50 degrees Celsius and the aorta's cooling effect of 37 degrees Celsius over the ablation time. FIG. 3B shows a graph of the resulting change in temperature as a function of the distance from the lumen of the aorta. The lumen is the inner space of the vessel. The planner can partly account for such heat sink structures by ensuring that the PTV actually extends up to the heat-sink area to a distance corresponding to a higher expected temperature. In FIG. 3C, the PTV 40 is adapted so that it is moved closer to the aorta, causing a distension 46 of the PTV. This can also be accomplished by adding a compensating "virtual PTV" by hand, which extends the PTV in the direction of the aorta, in a location based on the expert opinion of the physician.

FIGS. 4A-D illustrate a plurality of graphical representations 60 of various actions associated with planning an ablation procedure for a patient with an otherwise inoperable tumor.

Figure 4C:
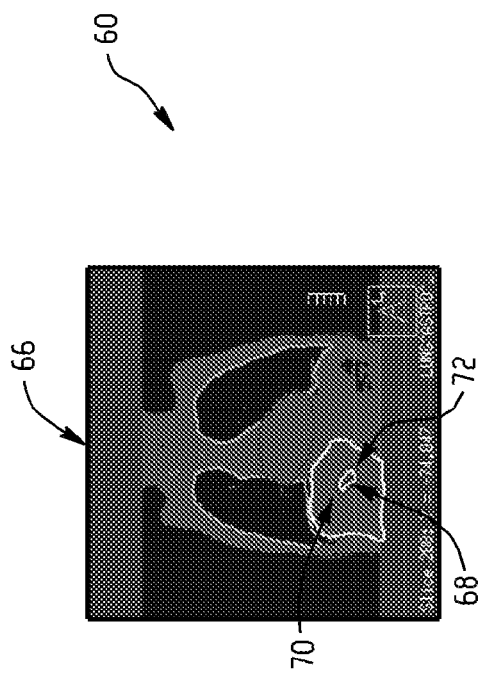
Figure 4B:
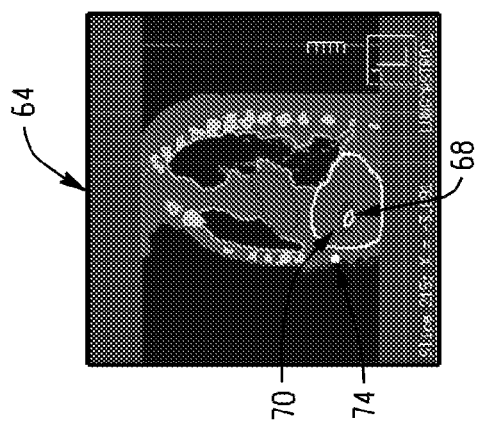
Figure 4A:
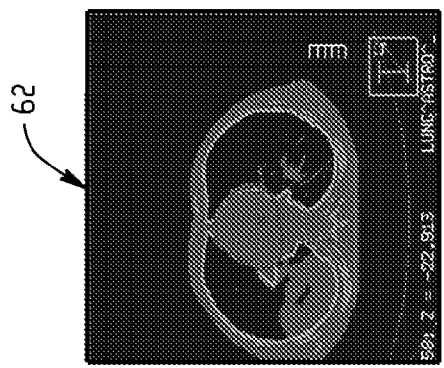
Figure 4D:
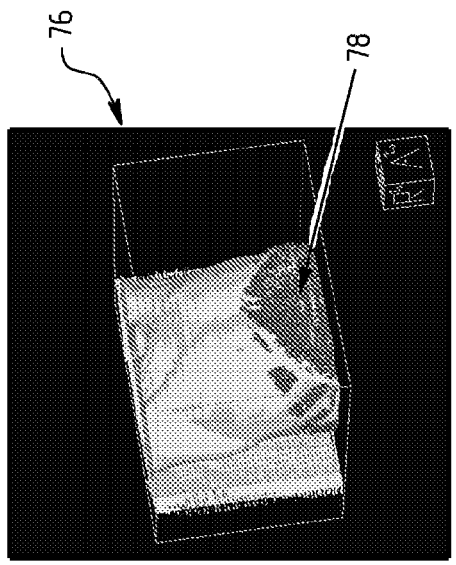

The graphical representations 60 include multiple views of a patient with an abdominal tumor, such as is generated using a magnetic resonance imaging tool or the like. In FIG. 4A, a CT image 62 illustrates an axial slice; image 64 shows a sagital view of the patient's thorax and upper abdomen; and image 66 illustrates a coronal view of the patient's thorax and upper abdomen.

A tumor mass volume 68 is segmented and enveloped by the planned target volume (PTV) 70, which is the visualized or otherwise calculated tumor mass 68 volume plus an additional safety margin, or buffer region 72, shown as the space between the tumor mass 68 and the perimeter of the PTV 70. The margin during surgery 72 is typically approximately 1 cm beyond the tumor, and can be verified by pathologists. A good surgical outcome is when the 'margins are clear', in other words, the outer edge of the surgically removed tumor is free from cancerous cells upon examination by a pathologist. When RF or other minimally invasive ablation techniques are used however, a pathologist is unable to assess the margins.

In essence, the margin attempts to compensate for different possible sources of error, but may be adjusted for particular patient anatomy and issues, such as if the treatment is palliative. Some of the sources of error include:
   patient motion between the time of imaging and intervention,
   difficulty defining the precise edges of the tumor,
   inability to image microscopic cancers surrounding a tumor,
   difficulty quantifying target ablation positions that cover the tumor and minimize collateral damage, and
   difficulty carrying out the procedure to the specific targets.
The margin is defined by the physician, but is usually approximately 1 cm, but can be anywhere between 0 and approximately 1.5 cm. Reducing the error in any of these ways can reduce the margin.

A set of possible skin entry points 78 and an orientation angle for the ablation probe to the tumor 68 center is calculated by routine 26 of FIG. 2, or alternatively the position and orientation can be entered manually by a physician. A single entry point 74 is illustrated in FIG. 4B. The skin surface point that indicates successful (e.g., safe) travel from the skin to the tumor 68 is shown by the darkened (previously red) area at arrow 78 in image 76.

FIG. 5 illustrates a methodology that is performed by optimization component 14 for generating an ablation planning solution, as discussed herein with regard to preceding figures and in accordance with various features. At 80, the routine 28 generates an initial set of candidate ablation ellipsoids to envelope a PTV for a tumor in a patient. The set of initial candidate ablation regions is generated using a greedy algorithm to achieve maximal coverage from N bounding sides. For example, in a case where N=6, the PTV is bounded by a box or cube with six sides. However, it will be appreciated that the PTV can be bounded by any suitable polyhedron (including but not limited to tetrahedrons, octahedrons, dodecahedrons, icosahedrons, Kepler-Poinsot solids, Archimedean solids, regular polyhedrons, irregular polyhedrons, etc.) in order to further optimize ablation planning and a number of ablations performed to eradicate a tumor and/or PTV.

At 82, a centering point, or centroid, is selected for the PTV, which may be the center of mass the tissue enveloped by the PTV (e.g., tumor mass plus buffer region). At 784, a determination is made regarding whether all candidate ablation ellipsoids have been visited, or evaluated. If it is determined at 84 that all candidate ablation ellipsoids have been evaluated, then the method jumps to 94, where a determination is made regarding whether all candidate ablation ellipsoids require re-evaluation. If determination at 94 is negative, then the method terminates. If the determination at 94 is positive, then the method reverts to 84 for reiteration of candidate ablation ellipsoid evaluation.

If it is determined at 84 that one or more candidate ablation regions requires evaluation, then at 86 a subsequent candidate is selected, and a unique coverage area (UCA) there for is determined. The UCA can be viewed as an area or region of the PTV that is enveloped only, or "uniquely," by the specific candidate ellipsoid volume being evaluated. At 88, a determination is made as to whether the UCA is equal to zero. If the UCA is equal to zero, then the candidate ablation ellipsoid in question does not cover any portion of the PTV that is not already covered by another candidate volume, and is removed from the candidate list at 90. The method then reverts to 84 for a determination of whether there are any remaining candidate ablation volumes to be evaluated.

If the determination at 88 indicates that the UCA for the candidate volume is non-zero, then the candidate is valid and retained in the candidate list and the method proceeds to 92. At 92, a point is identified that represents a closest position to the centering point selected at 82 that the candidate ellipsoid center can occupy while still enveloping the UCA. It will be appreciated that the identification of the closest potential ellipsoid center position to the centering point that still permits the ellipsoid to envelop the UCA can be further constrained to ensure that the ellipsoid ablation region does not envelop a critical region, such as a bone or other area that can harm the patient if ablated.

If the ellipsoid center is not already at the identified point, then the candidate ellipsoid is moved, which triggers a re-evaluation of all candidate ellipsoids still in the candidate list. At 94, a determination is made regarding whether all candidates in the list are to be re-evaluated. If so (e.g., if one or more candidates in the candidate list was moved), then all candidates are revisited at 96, and the method reverts to 84 for further iteration and optimization of the ablation planning solution. When all candidates' centers are as close to the centering point as possible while still covering their respective UCAs, the solution has stabilized and the routine terminates.

In accordance with other features, functional data related to, for instance, tumor density and/or growth activity can be considered when planning and optimizing ablation points. For instance, if the density of the tumor is greater in one region than in another, the denser region may require more ablation than the less dense region. According to another example, a portion of the tumor exhibiting more rapid growth than the rest of the tumor may be identified and targeted for more aggressive ablation than the rest of the tumor to ensure that it is eradicated. Thus, functional data related to the tumor can be employed when optimizing an ablation plan in order to account for relative strengths and weaknesses in the tumor mass.

Still other variations include performing adaptive planning techniques during optimization, which include, without being limited to, consideration of a priori knowledge of proximity of and/or distance between a critical region and the PTV, ablation temperature and duration for a given probe as a function of functional data associated with the mass, effects of heat sinks located near the PTV (e.g., structures that will draw heat from the ablation region and thereby affect ablation of the PTV), etc.

FIG. 6A image 100 illustrates a 3D segmented, irregular shape tumor with margin defining a PTV 102. The size and irregularity of the shape of the PTV poses a problem for conventional ablation procedures, since it cannot be completely covered by a single ablation of this size. Even if a sufficiently large ablation was possible, it would simultaneously cause a large amount of collateral damage, killing healthy tissue, if not ideally shaped. Since there are a finite number of ablation probes, each with fixed ablation zones, the task is to simulate each of the possibilities so that the best probe can be selected. However, as illustrated by image 106 in FIG. 6B, a plurality of ellipsoid ablation regions 108 are computed, for a given ablation probe. Determining the ellipse centers to cover the PTV 102 correlates to routine 28 of FIG. 2, described above.

The first set of ellipses 108 is generated to cover the largest possible "bites" corresponding to the ablation volume of the PTV. In one embodiment, a bounding box or cube is defined about the PTV and a point of tangency on each of the six faces of the PTV's bounding box. The largest bite, which covers a maximum number of PTV voxels (e.g., volumetric pixels that represent a points in 3-D space), is selected from the six points, and the corresponding voxels are deleted from the PTV to be covered. This action is iteratively repeated until the PTV has no more uncovered pixels. The ellipses generated up to this point are the candidate ellipses for ablation.

A point within the PTV 102 is selected, e.g. the center of mass, called the centering point 104. Routine 28 visits each ellipse in the list of candidate ellipses in turn. For each candidate, a unique volume that the ellipse contributes to the coverage, called the Unique Coverage Area (UCA), is determined. If the UCA is zero (0), then the ellipse does not cover any unique portion of the PTV 102, which can be due to the movements of other ellipses. When this occurs, the ellipse having the null UCA is removed from the candidate list, and the next ellipse evaluated. If the ellipse has a non-zero UCA, a binary search is performed to test locations between the current ellipse center and the centering point 104 of the PTV 102 to find the location nearest to the centering point 104 where this ellipse can be moved, while still covering the UCA. Moving ellipse centers toward the centering point 104 ensures that the entire tumor mass is ablated while minimizing undesired ablation of tissue surrounding the tumor. That is, moving the ellipse centers toward the centering point 104 shrinks the PTV 102 to fit the tumor while minimizing damage to healthy tissue near the perimeter of the PTV 102. If any of the ellipses is able to be moved closer to the centering point 104 of the PTV 102 while still covering its UCA, then the positions of all candidate ellipses are re-examined. When no ellipse centers can be moved closer to the centering point 104 of the PTV 102 without compromising the coverage of their respective UCAs, the ablation planning solution has stabilized. Optionally, this process can be repeated with the initial set of covering ellipses results in a smaller number of ellipses.

In FIG. 7, an image 110 of a plurality of the ellipsoid ablation volumes 108 each ellipsoid have a center 114, which is determined as described above with regard to the preceding figures, and has a known volume that is a function of the selected probe size and ablation duration.

With reference to FIG. 8, an ablation pattern for an ablation probe 120 is depicted by the elliptical region 124. The ablation probe 120 is inserted into a tumor mass or PTV in a patient along a selected trajectory from an insertion point on the skin to the PTV to facilitate ablation of all or a portion of the PTV. According to an example, the target location for the probe tip is beyond the midpoint of the ellipsoid, and therefore the position of the probe tip is controlled to a distance 122 beyond the ellipse center 114 to ensure that the ablation occurs in the desired position. It will be appreciated that distance 122 typically varies from probe to probe and is not intended to be limited to the actual and/or scaled distance represented in FIG. 6.

FIG. 9A illustrates computer-modeled images of a PTV and candidate ellipsoid ablation volumes that overlap a critical region 136, such as a bone. For instance, in a scenario in which the critical region is so difficult to access that, without extraordinary effort, some small portions of the tumor cannot be reached, actions are performed to ensure that the critical region 136 is not ablated while keeping a number of ablations to a minimum. In the image 130, an area 134 encompasses a plurality of areas that are that are too close to a critical region 136 to permit ablation. In image 132 (FIG. 9B), the unablatable areas are presented to a physician (e.g., via the GUI 18 or the like) as being highlighted so that the physician can take appropriate action. For example, the physician can select a different ablation probe. In this example, a smaller probe with a smaller ablation ellipsoid volume is selected whose ellipsoid volume does not intersect the highlighted critical volume. According to another example, the physician injects saline into a space between the tumor and the critical region 136 to separate the tumor from the critical region 136. If a different probe for one or more of the ablations is selected, the optimization routine 28, FIG. 2 is advantageously repeated. Similarly, if saline is injected to increase a space between the tumor and the critical region 136, the PTV is reevaluated and the optimization routine 28 is repeated to account for changes caused by the saline injection.

FIG. 10 illustrates a method that is performed by optimization component 14 for planning an ablation procedure, in accordance with some embodiments. The method permits ablation volumes to be pulled toward a centroid point as though by gravity, which facilitates minimizing over-ablation of tissue outside of a typical lesion, while providing the potential for overlapping regions to consolidate. The method can further reduce the number of ablation volumes by creating additional "gravity centers," or points, that further reduce the number of ellipses.

At 140, a number of "gravity points" are determined. At 142, a determination of whether there are more candidate ablation volumes to analyze is made. If there are no further candidate ablation volumes to evaluate, then the method terminates. However, if one or more other ablation volumes remain to be evaluated, then at 144 the next candidate is selected, and a UCA there for is define and/or determined. At 146, a determination is made regarding whether the UCA is equal to zero (e.g., the candidate does not have a unique coverage area). If so, then at 148 the candidate is removed from the list and the method reverts to 142. If the candidate has a UCA, then at 150, a nearest gravity point to the candidate ablation volume's centroid is determined.

At 152, an ablation volume nearest to the gravity point while still covering the UCA is identified. If the ablation volume is moved to ensure that the UCA is still covered, then a "revisit all candidates" condition is true. At 154, a determination of whether the "revisit all candidates" condition is true is made, and if so, then the list of candidate ablation volumes is revisited in total, at 156. In this case, the method repeats. If no candidate ablation volume has been moved, then the method terminates.

The following discussion provides an example of a manner in which gravity points are determined A "tumor-to-ablation" factor (TAfactor) can be defined as spherical tumor radius/ spherical ablation radius. Thus, when TAfactor is less than or equal to 1, one ablation will cover the tumor. When 1<TAfactor<=1.25, then six ablations cover the tumor. When 1.25<TAfactor<=1.66, then 14 ablations cover the tumor, and so on. Since the method permits ablation planning for arbitrarily shaped tumors, it can be desirable to use the more general and flexible ellipsoid for the ablation shape rather than a sphere, since ablation regions are often ellipses, but can also be spheres (an ellipse with equal a,b,c axes). The following example, for simplicity, describes the procedure with two different sized spheres for the tumor and ablation.

An important difference between this method and the method of FIG. 5 is the identification of "gravity points," which pull the ablations from the center toward a collection of regional nodes, where they can be further aggregated to minimize the number of ablations. The gravity points for a set of 6 spheres (1 <TAfactor<=1.25) are located, for example, at a distance Q of 0.76*ablation-radius from the center of the tumor along each of the X, Y and Z axes (in both+ and − directions). For example, if the tumor has a radius of 2.5, and the ablation has a radius of 2, then the TAfactor is exactly 1.25. The locations of the gravity points are therefore Q=0.76*2 =1.52 away from the center of the tumor along each of the 3 axes. If the tumor were centered at (0,0,0), then the gravity points would be located at: (0,0, 1.52), (0,0,−1.52), (0, 1.52,0), (0,−1.52,0), (1.52,0, 0), (−1.52,0,0).

The gravity points for a set of 14 spheres (1.25<TAfactor<=1.66) are a combination of 6 spheres located along the x,y,z axes and 8 more that fill the 'corners' between them. The first 6 are at a farther distance W=0.90*ablation-radius, from the center of the tumor. For example, if the Tumor has a radius of 3.32, and the ablation has a radius of 2, then the TA factor is exactly 1.66. Calculated similarly, the first 6 are located W=0.9*a=1.8 from the center of the 3.32 radius tumor. The remaining 8 gravity points are at the diagonals. These are formed by equal, absolute distances along two different axes. The absolute distance $L=W^2$ sqrt(1/2). In this example, $L=(1.8)^2$ sqrt(1/2)=3.24*0.07071=2.291. The diagonals are located at the following locations for a sphere: (L,L,L), (L,L,−L), (L,−L,L), (L,−L,−L), (−L,L,L), (−L,L,−L), (−L,−L,L), (−L,−L,−L). Where (1.25<TAfactor<=1.66), the first consolidation can be performed to draw the ablation centers toward the very center, as described above, and then the steps of FIG. 10 can be executed to draw them toward the nearest of the gravity points.

This technique can be used advantageously if the tumor is circumscribed by a sphere, thus making it somewhat more general, and when the ablation probe generates a spherical ablation volume. The technique can also be used when the TAfactor is >1.66. This is especially true when the tumor is circumscribed by a sphere, and the current practical limit for number of ablations is limited not only by the 15 minutes required per ablation, but also in the accuracy of placement. As ablation techniques become faster, probe placement can be guided with imaging or tracking to improve accuracy.

In practice, the tumor can be an arbitrary shape and the ablation shape can be arbitrary. In these situations, the gravity points can be determined by inscribing the tumor in a sphere and inscribing the ablation in a sphere. The ratios of the radii can be used to define the TA factor and to calculate gravity points. This simplicity enables the technique to compute quickly, while adapting to arbitrary shaped tumors and ablations. A quick computation then allows multiple scenarios to be evaluated, so that entry points with the fewest ablations, and/or the least collateral damage, can be identified.

Alternatively, more sophisticated computations can be used to define gravity points where the PTV is enclosed by a sphere, and the elliptical ablations are calculated to cover the sphere. The centroids of possibly many ellipses that cover the sphere are the gravity points.

According to another embodiment, step 80 from FIG. 5 can be performed to create the initial ablations, and can be followed by the steps of FIG. 10. This technique can be effective in a large number of cases, however in other cases it is preferable to perform both the steps of FIG. 5 and then the steps of FIG. 10. For example, for spiculated (spiked) lesions, characteristic of some breast cancers and others, condensing the coverage to the center and then re-distributing it, can reduce the overall number of ablations.

FIGS. 11 and 12 illustrate an abnormally-shaped PTV 170 that is to be covered by an ellipsoid ablation 172, such as may be utilized as the ellipsoid ablation volumes in the techniques of the preceding figures. The ellipsoid ablation has radii a,b, c=36,17,17, which define a centroid of the ellipsoid ablation volume. The ablation volume is scaled (e.g., by the processor 21 and/or the optimization component 14 of FIG. 1) by multiplying each radius by a predetermined factor. For instance, the predetermined factor may be 1.3, in which case the ablation 172 has radii of $a_s$, $b_s$, $c_s$=1.3*a,b,c=46.8, 22.1, 22.1, respectively. In this manner, a 3D ablation shape is approximated by an ellipsoid, having radii or half-lengths a,b,c of the major axes, and adjusted to cover the PTV 170. That is, a PTV having a random shape is covered by an ellipsoidal shape at the same orientation as the 3D ablation, which is properly scaled. This is achieved by first taking the centroid of the ablation, and finding the largest scale that encloses or covers the PTV.

In this manner, the system of FIG. 1 is employed to provide affine scaling of ablation shape to cover an arbitrary PTV. There are two aspects to transforming the problem of covering an arbitrary PTV with ellipsoidal ablations into that of covering a sphere with smaller spherical ablations. The converted problem involves determining a sphere that completely encloses the arbitrary PTV, and determining a relative configuration of smaller spheres that covers the enclosing sphere. The described technique uses prior knowledge (such as may be generated using the techniques described in Radiofrequency Thermal Ablation: Computer Analysis of the Size of the Thermal Injury Created by Overlapping Ablations, Dodd et al., AJR 177, October, 2001, which is hereby incorporated by reference in its entirety) of relative-configurations of 6 or 14 spheres that completely cover a sphere of a related size. The number of smaller spheres (e.g., 6 or 14) depends upon the ratio of the enclosing sphere to the smaller sphere(s), and the exact configuration is also related to the size of the larger enclosing sphere.

Thus, a model is created for covering the arbitrary PTV with either 6 or 14 ellipsoidal ablations by transforming the ellipsoidal coverage problem to the sphere-coverage domain. For instance, a one-scaled ellipsoid-shape is determined, which has the same relative dimensions and orientation of the template ellipsoid-shape ablation that completely covers the arbitrary PTV. The exact location of the center of the ellipsoid can be found by a simple minimization algorithm. A scaling of the template ellipsoid-shape is then applied: assuming (a, b, c) are the radii of the template ellipsoid-shape ablation; two independent scale factors are applied, k1 and k2, to two of those radii in order to produce a spherical template ablation shape with radius r. The same scale factors, k1 and k2, can now be applied on the ellipsoid-shape (that covers the arbitrary PTV) as well as the PTV, in effect producing a sphere of radius R that circumscribes the scaled PTV. Use of a simple scale transform ensures that the scaled sphere of radius R encloses the scaled PTV just as the ellipsoid-shape completely covered the arbitrary PTV. The center of that circumscribing sphere is the reference point related to the PTV when determining the relative configuration of smaller spheres that covers the enclosing sphere. The scale factor (R/r) determines how many smaller spheres are required to cover the enclosing sphere circumscribing the PTV. The known coverage solutions, which use 6 or 14 spherical ablations, can be used to guarantee coverage of this circumscribed PTV. A 6-ellipsoid solution can be found for scale factors between 1 and approximately 1.25, a 14-ellipsoid solution can be found for scale factors between approximately 1.25 and approximately 1.66. Larger scale factors may require larger number of.

The relative configuration of the smaller ablation spheres is also known and is related to the radius R. In the sphere configuration, the centers of the smaller spheres are symmetrically grouped around the center of the larger enclosing sphere. The relative configuration of the smaller spheres is transformed back into the ellipsoid shape by applying the inverse of the two scaling factors used earlier to the respective x/y/z centers of the spheres relative to the reference point. This step transforms the smaller spheres back into the true ellipsoid-shaped ablations and the circumscribing or enclosing sphere back into the circumscribing ellipsoid that covers the arbitrary PTV.

FIG. 13 illustrates the abnormally-shaped PTV 170 after circumscription by a scaled ablation, which can be performed quickly. A bounding box 174 is placed around the PTV 170. The half-lengths of the bounding box form the $a_{PTV}$, $b_{PTV}$, $c_{PTV}$ of the PTV (e.g., 17.5, 17, 22.1), and define a spheroid ablation volume that covers the PTV. A largest relative fraction (e.g., the predetermined factor value) is determined between the PTV and the ablation volume. In one example, max $\{a_{PTV}/a, b_{PTV}/b, c_{PTV}/c\}$=1.3.

FIG. 14 illustrates a 6-ablation solution 180 selected to cover the sphere for values between 1 and 1.25. The solution 180 comprises 6 spherical ablations 182.

FIG. 15 illustrates a 14-ablation solution 190 selected to cover the sphere for values between 1.25 and 1.66.

FIG. 16 illustrates a 14-ablation solution 200 comprising 14 ellipsoidal ablations 202 after application of the predetermined factor to the ablation spheres 182 of FIG. 15. A layout for ellipsoidal ablations is determined by taking the appropriate spherical coverage scenario (e.g., the 14-ablation solution, for the DoddFactor=1.3) and scaling it according to the fraction of the center sphere, considered as a=b=c=1, to the base ablation, a=36,b=17,c=17 to create a set of covering elliptical ablations. This particular example illustrates one of the worst-case scenarios, where the ellipses are oriented horizontally, but the major axis of the PTV is vertical. However, the layout of this initial set of ablations can be performed nearly instantly.

Once the ellipsoid ablations 202 have been generated, they can be manipulated using the methods described with regard to FIGS. 2, 5, and 10. E.g., the ellipsoid ablation regions 202 are treated as candidate ablation regions for optimization in a manner similar to the candidate ablation regions 108 of FIG. 7.

FIGS. 17 and 18 illustrate examples of ablation building blocks, such as may be generated by the BBG 22 of FIG. 1. For instance, FIG. 17 illustrates an example of a pull-back simple building block (SBB) 210 consisting of 3 spherical ablations, which define a tube of diameter 212, i.e., the diameter at the intersection of adjacent spheres. FIG. 18 shows how 4 SBBs can be used to build a total building block (TBB)

220 to cover a PTV consisting of 2×2×3 cubes defining a rectangular prism of width 222, height 224, and length 226.

In one embodiment, multiple sequential ablations are represented as a building block. The assumption is that these are like a "recipe" and easier to perform for an interventional radiologist (IR). These building blocks can be, e.g., an extended cylinder shape, which can be construed as the largest inscribed cylinder in a composite set of ablations. In another example, the building blocks have a composite ellipsoid/sphere shape, e.g., two or more ellipsoids/spheres displaced by a fixed distance along the long-axis (axial pullback method), or two or more ellipsoids/spheres displaced laterally by a fixed-distance (side-by-side).

The TBB shape is the union of a user-specified number and placement (relative) of SBB shapes. The SBB shape can be used as the template ablation shape that is repeatedly placed at various locations inside the PTV using the algorithm described with regard to FIG. 1-10, or a manual placement tool. Alternatively, for larger tumor coverage, the TBB shape can also be used as the template ablation shape.

The primary input for all variants of the building block generator is the 3D geometry (size and shape) of the individual ablation created by the ablation device to be used. For manual building block generation, a user can either select in a GUI or define freely the geometry of the building block (pull-back; side-by-side; etc.), the number of individual ablations, and the spacing between ablations in the building block. Also, the user can determine if the TBB or SBB is to be calculated. If the SBB is chosen, the user may determine which "simple" shape (sphere, ellipsoid, cylinder, cube . . . ) is to be used for approximation of the building block.

For semi-automatic building block generation, the user may choose some parameters such as the geometry of the building block (e.g., pull-back) and the number of ablations per building block, but other parameters are determine automatically (e.g., the optimal spacing between individual ablations in the building block may be determined by maximizing the volume of a cylinder that can be fully inscribed, as in FIG. 17).

For automatic building block generation, the PTV to be covered is an additional input parameter to the BBG. The BBG operates in conjunction with the ablation planning algorithm or system 10 to determine the optimal building block for a specific PTV, given a selection of possible building block geometries and a possible range of numbers of ablations per building block. For example, the BBG 22 may generate pull-back building blocks with 2, 3, and 4 ablations, calculate the coverage of the PTV (i.e. the ablation plan) for each building block, determine the total procedure time for each solution, and return the building block that results in the minimum procedure time as the optimal building block for the specific PTV.

Additional considerations for automatic building block generation and planning include the number of ablations per building block and/or the spacing between individual ablations in a building block may be determined by the size of the PTV measured along the direction of the ablation probe axis (i.e. projection of PTV on probe axis). The BBG 22 may determine the shape and/or geometry of the building block, and the size/number of ablations per building block may be variable during the coverage planning phase. For example, the chosen shape may be "pull-back," and the spacing between ablations in the pull-back is determined by maximizing the volume of a cylinder that can be fully inscribed, and the number of ablations is variable during the coverage planning phase such that fewer pull-back ablations are performed in "thinner" regions of the PTV and more pull-back ablations are performed in "thicker" regions of the PTV. Here, "thin" and "thick" refer to the size of the PTV measured along the direction of the ablation probe axis.

Specific SBBs may have specific implications in the coverage planning phase for the relative placement of building blocks. For example, pull-back building blocks may be spaced laterally at such a distance as to maximize the volume of inscribed cubes 228, as in FIG. 18. This constraint greatly reduces computational complexity and thus computation time for the coverage planning solution. In this manner, the advanced ablation planning system 10 (FIG. 1) provides treatment plans based on coverage of the PTV with a minimum number of a variety of "building blocks", instead of trying to cover the PTV with a (significantly larger) number of arbitrarily placed individual ablations. FIG. 19 is a graph 230 with two curves that show that collateral damage is significantly smaller than what would be obtained if the axial or diagonal distances were not adjusted with a reduced ablation radius, such as may be achieved using the CD minimization component 24 (FIG. 1). A first curve 232 shows collateral damage for a 6-ablation solution, and a second curve 234 shows collateral damage for a 14-ablation solution.

In one embodiment, a lookup table is employed to tighten a known configuration of ablation spheres to cover an enclosing sphere that encompasses an arbitrary PTV. This approach involves using analytical results for locations of 6 or 14 spheres that are tightened around the PTV to reduce the collateral damage for covering a spherical PTV that is in between the prescribed limits. When an arbitrary PTV is enscribed be the enclosing sphere, the technique can be employed to tighten a known spherical configuration on the enclosing sphere, thereby covering the arbitrary PTV.

Prior knowledge (e.g., generated using the Dodd technique) of relative-configurations of 6 or 14 spheres that completely cover a sphere of a related size is employed in this approach. The number (e.g., 6 or 14) depends upon the ratio of the larger enclosing sphere to the smaller sphere, and the exact configuration is also related to the size of the larger sphere. If the scale factor is in the range of approximately 1.0–1.25, the configuration as specified by the limit of 1.25 is sufficient to cover all PTV's that lie within the range of 1.0–1.25. However this may not be optimal in terms of collateral damage. A better configuration of 6 ablation spheres that has lesser collateral damage can be determined in terms of analytically computed centers, as described herein. The same is true for the 14 sphere configuration.

There are additional known sphere configurations (e.g., starting with a 4-sphere configuration in a tetrahedral arrangement), as described in Khajanchee, that are also amenable to globally scaling the locations of the centers of each ablation sphere towards the center of the PTV, to reduce collateral damage.

Regardless of the method by which the ablation volumes are scaled, the resulting centers of the spherical ablations can be further tightened using the algorithms of described herein with regard to FIGS. 1-10, to cover the arbitrary PTV shape.

One advantage of known analytical solutions to the problem of covering a spherical PTV with spherical ablations for known configurations is that it is known that if the radius of the PTV (sphere) is 1.25 times the radius of the ablation (also a sphere), then it takes exactly 6 ablations to completely cover the PTV. If the ratio is larger than 1.25, it will take more than 6 ablations. Similarly, if the radius of the PTV is 1.66 times the radius of the ablation, then it takes exactly 14 ablations to completely cover the PTV. These solutions are also the minimal number of spherical ablations to cover the PTV but for only those specific ratios, meaning that it may be possible to find fewer than 6 spherical ablations to cover a PTV whose radius is less than 1.25 times the radius of the ablation, or less than 14 spherical ablations to cover a PTV whose radius is in between 1.25 and 1.66 times the radius of the ablation.

The use of the term "solutions" in this context refers to the exact specification of the centers of the ablation spheres with respect to the center of the PTV sphere in a specified coordinate system. Without loss of generality, the PTV is assumed to be centered at the origin (0, 0, 0) of the coordinate system, its radius is assumed to be $R_p$, and the radius of the ablation sphere is assumed to be $R_a$ (arbitrary units mm, cm, etc.), for ratios $R_p/R_a > 1.0$. If the PTV is smaller than the ablation, the solution is to simply place one ablation center or centroid at the center of the PTV.

The known solution to the 6-sphere coverage problem comprises placing one ablation sphere on each of the three coordinate axes at a distance $R_a/\sqrt{2}$ from the origin of the PTV. The 3D (x, y, z) coordinates of the centers of the ablation spheres are then:

1. Ablation 1: $\left(R_a \frac{1}{\sqrt{2}}, 0, 0\right)$

2. Ablation 2: $\left(-R_a \frac{1}{\sqrt{2}}, 0, 0\right)$

3. Ablation 3: $\left(0, R_a \frac{1}{\sqrt{2}}, 0\right)$

4. Ablation 4: $\left(0, -R_a \frac{1}{\sqrt{2}}, 0\right)$

5. Ablation 5: $\left(0, 0, R_a \frac{1}{\sqrt{2}}\right)$

6. Ablation 6: $\left(0, 0, -R_a \frac{1}{\sqrt{2}}\right)$

This solution provides complete coverage of a PTV whose radius $R_p < 1.25 \times R_a$. It will be noticed that the distance between the center of the ablation to the center of the PTV is identical for all ablations, i.e. the ablations are symmetrically placed around the PTV. This distance (axial distance) can be treated as a parameter for further optimization by the system 10 of FIG. 1.

The known solution to the 14 sphere coverage problem is using the locations on the coordinate axes for the first 6 spheres described above, except at a distance $R_a$ from the origin. The 8 additional spheres are located along the diagonal direction at a distance of $R_a\sqrt{3}/\sqrt{2}$ from the origin. The 3D (x, y, z) coordinates of the centers of the ablation spheres are then:

1. Ablation 1: $\left(R_a \frac{1}{\sqrt{2}}, 0, 0\right)$

2. Ablation 2: $\left(-R_a \frac{1}{\sqrt{2}}, 0, 0\right)$

3. Ablation 3: $\left(0, R_a \frac{1}{\sqrt{2}}, 0\right)$

4. Ablation 4: $\left(0, -R_a \frac{1}{\sqrt{2}}, 0\right)$

5. Ablation 5: $\left(0, 0, R_a \frac{1}{\sqrt{2}}\right)$

-continued

6. Ablation 6: $\left(0, 0, -R_a \frac{1}{\sqrt{2}}\right)$

7. Ablation 7: $\left(R_a \frac{1}{\sqrt{2}}, R_a \frac{1}{\sqrt{2}}, R_a \frac{1}{\sqrt{2}}\right)$ 8. Ablation 8: $\left(R_a \frac{1}{\sqrt{2}}, R_a \frac{1}{\sqrt{2}}, -R_a \frac{1}{\sqrt{2}}\right)$ 9. Ablation 9: $\left(R_a \frac{1}{\sqrt{2}}, -R_a \frac{1}{\sqrt{2}}, R_a \frac{1}{\sqrt{2}}\right)$ 10. Ablation 10: $\left(R_a \frac{1}{\sqrt{2}}, -R_a \frac{1}{\sqrt{2}}, -R_a \frac{1}{\sqrt{2}}\right)$ 11. Ablation 11: $\left(-R_a \frac{1}{\sqrt{2}}, R_a \frac{1}{\sqrt{2}}, R_a \frac{1}{\sqrt{2}}\right)$ 12. Ablation 12: $\left(-R_a \frac{1}{\sqrt{2}}, R_a \frac{1}{\sqrt{2}}, -R_a \frac{1}{\sqrt{2}}\right)$ 13. Ablation 13: $\left(-R_a \frac{1}{\sqrt{2}}, -R_a \frac{1}{\sqrt{2}}, R_a \frac{1}{\sqrt{2}}\right)$ 14. Ablation 14: $\left(-R_a \frac{1}{\sqrt{2}}, -R_a \frac{1}{\sqrt{2}}, -R_a \frac{1}{\sqrt{2}}\right)$ This solution provides complete coverage of a PTV whose radius $1.25 \times R_a < R_p < 1.66 \times R_a$. It will be noted again that 6 of the ablations are at a fixed distance from the center of the PTV and the other 8 ablations are at another fixed distance from the center of the PTV. These two distances (axial and diagonal distance) can be treated as parameters for further optimization.

The problem with known solutions is that they cause more collateral damage than an optimal location of the 6 spheres that could be tightly placed around the PTV to completely cover the PTV and to minimize collateral damage to healthy tissue. In a similar sense, the classical 14-sphere solution specified above is also the simplest analytically computable solution to cover a spherical PTV whose radius is greater than 1.25 times the radius of the ablation but less than 1.66 times the radius of the ablation, but it is also non-optimal with regard to collateral damage. The CD minimization component 24 identifies such analytically computable solutions for covering an arbitrary shape PTV while minimizing collateral damage to surrounding non-tumor tissue using axial and diagonal distance as parameters for optimizing the location of the ablation spheres.

The CD minimizer 24 exploits the use of analytically computed solutions for placing spherical ablations to completely cover an arbitrarily-shaped PTV with minimal collateral damage to surrounding tissue based on the insight that to cover an arbitrarily-shaped PTV with spherical ablations, it is sufficient to first compute the smallest circumscribing sphere that covers the PTV, and second to apply the known sphere coverage solutions to cover the circumscribing sphere. Covering the circumscribing sphere is equivalent to covering the original PTV, which lies completely within the circumscribing sphere. The ratio of the circumscribing sphere radius to the ablation sphere radius provides guidance in whether to use the 6-sphere solution or the 14-sphere solution.

Additionally, the CD minimizer 24 adapts the known geometrical configuration using the two distance parameters (axial and diagonal distance) as variable parameters to calculate an improved placement for the 6- or 14-sphere solutions specified above. After computing a spherical coverage solution to the circumscribing sphere, the CD minimizer applies a tightening function towards the center of the PTV to minimize collateral damage for the actual PTV shape, rather than the circumscribing sphere for which the spherical coverage solution was computed. The tightening step utilizes the notions of unique coverage area as described with regard to preceding figures, but to each of the spherical ablations. Any unnecessary ablations that do not contribute to the unique coverage of the PTV can be eliminated.

Circumscribing an arbitrary three dimensional shape with a minimal sphere is performed using known techniques, such as a "Smallest Enclosing Ball of Points" technique. For example, to cover a PTV circumscribed with a sphere whose radius is $R_p=2$ cm, with ablation spheres of radius $R_a=1.81818$ cm, to use known solutions with the PTV to ablation radius ratio being 1.1 it is necessary to position 6 spheres, but it is not necessary to place the 6 spheres at a distance of $R_a/\sqrt{2}$ from the origin of the PTV. Knowing that the placement of the 6 spheres is $R_a/\sqrt{2}$ only at the boundary condition of $R_p/R_a=1.25$, and that only one sphere is needed if the ratio $R_p/R_a=1.0$ (i.e. mathematically the distance of all 6 spheres from the origin is 0); we can use a simple linear interpolation to calculate the axial distance at which to place the spheres as:

$$\text{Axial Distance} = 0.75 \frac{(R_p - R_a)}{(R_p - R_p/1.25)} \frac{R_a}{\sqrt{2}}$$

The factor 0.75 is chosen to further reduce the collateral damage across the range of ratios from 1.0 to 1.25; however the ratio at which the coverage of the PTV is lost is somewhat reduced from 1.25. To illustrate this effect for the example chosen earlier, with $R_p=2.0$ cm, $R_a=1.81818$ cm, the Axial Distance at which to place the 6 ablations is $0.341*R_a/\sqrt{2}$, which is significantly smaller than $R_a/\sqrt{2}$ and therefore the collateral damage is correspondingly much smaller.

However, if the 0.75 factor is selected, a sphere with radius $R_p=2.0$ cm is covered completely with ablation radii greater than 1.65 cm. This implies coverage of the PTV with 6 ablations is no longer possible at $R_p/R_a=1.25$, but rather that the ratio becomes $R_p/R_a=2/1.65=1.21$. This is a small trade off for the reduced collateral damage that is obtained across the range of ratios extending from 1.0 to 1.21. In a similar manner, for the 14-sphere solution configuration, the axial distance is tightened, as well as the diagonal distances, independently for covering ratios of $1.25<R_p/R_a<1.66$, and the two distance parameters can be set using a form of linear interpolation as follows:

$$\text{Axial Distance} = 0.75 \frac{(R_p - R_a)}{(R_p - R_p/1.25)} \frac{R_a}{\sqrt{2}}$$

$$\text{Diagonal Distance} = 0.40 \frac{(R_p - R_a)}{(R_p - R_p/1.25)} \frac{R_a}{\sqrt{2}}$$

The two factors 0.75 and 0.40 are chosen to further reduce the collateral damage across the range of ratios from 1.25 to 1.66; however the ratio at which the coverage of the PTV is lost is somewhat reduced from 1.66. FIG. 19 illustrates the resulting collateral damage as a percentage of the circumscribed sphere volume for the b- and 14-sphere configurations for the specific case of a PTV circumscribed by a sphere of radius $R_p=2.0$ cm, to be covered by ablation spheres ranging from a radius of 1.2 cm to 2.0 cm. The 1.2 cm ablation radius theoretically requires 14 ablations to completely cover the circumscribing sphere, but the minimum ablation radius that obtains complete coverage of the PTV with the 14 ablation configuration is $R_a=1.25$ cm. This implies coverage of the PTV with 14 ablations is no longer possible at $R_p/R_a=1.66$, but rather that ratio becomes $R_p/R_a=2.0/1.25=1.60$. Again this is a small trade off for the reduced collateral damage that is obtained across the range of ratios extending from 1.20 to 1.60.

The two curves in FIG. 19 show that the collateral damage is significantly smaller than what would be obtained if we the axial or diagonal distances were not changed with reduced ablation radii. The linear proportionality formula as shown above is a useful benchmark in itself. Other possible formulations for optimizing the axial and diagonal distances can be determined through nonlinear minimization techniques (e.g. Nelder Mead Simplex method, Powell's method, Levenberg Marquardt method, etc.)

The ablation "tightening" step in this algorithm is similar to that described in FIGS. 5 and 10 except that the ablations are now spherical in nature and are initially distributed along the axial or diagonal directions only. This initial solution can be used to start the algorithm for movement and tightening of the cluster of ablations as described with regard to FIGS. 5 and 10.

FIGS. 20 and 21 illustrate ellipsoidal ablations with identically oriented ablations covering a PTV 240, and with variably oriented ablations covering the PTV, in accordance with various aspects described herein. As described with regard to FIGS. 1-10, each ablation in the cluster is oriented along the line connecting the entry point on the skin to the centroid of the PTV, which assumes the ablations are identically oriented regardless of the actual relationship of the size and shape of the PTV and its proximity to the entry point on the skin. In FIGS. 20 and 21, the systems and methods described herein account for the possibility of each ablation having an orientation that is determined by the line connecting a fulcrum point to the actual center of the ablation. The fulcrum point may be the RFA needle entry point on the patient's skin surface; however it may also be a point slightly inside the body, such as the liver capsule. Interventional radiologists who conduct RFA procedures may prefer to have an invariant fulcrum point across all ablations, since it minimizes trauma to the patient as well as overall complexity of the procedure. IN such a scenario, the needle is directed into each new ablation center position by a slight retraction of the needle tip from its current ablation center position, pivoting around the fulcrum point by exerting a slight force in the direction opposite to the next target position of the needle tip, and followed by a slight insertion of the needle tip into the next ablation center position. The fulcrum point needs to be chosen before the automated ablation coverage algorithm is executed.

FIG. 20 shows a PTV 240 being covered by multiple ellipsoidal ablations 242 with identical orientation. If the orientation axis of each ablation is extended upwards (towards the patient skin for example) it is obvious that the orientations are all parallel to each other. Executing an RFA plan with this cluster of ablations will require several skin entry points.

Voxel coverage of multiple side-by-side ablations placed using a single entry point to cover a PTV can be made more accurate when executed using the fulcrum technique. IN this embodiment, the planning algorithm, when determining coverage of the PTV, takes into account the actual orientation of the ablation as placed. The template ablation shape includes only a shape and size, but the orientation is different for one or more ablations. The computed RFA plan accurately predicts the composite ablation shape. This technique is not limited to ellipsoidal ablations, but rather applies to arbitrary shapes as well.

FIG. 21 shows a PTV 240 being covered by multiple ellipsoidal ablations 242 with variable orientations determined by a fixed fulcrum point that lies on the patient's skin surface. All ablations are therefore realizable with a single fulcrum point to define a conical or truncated conical ablation region. The solution computed by the ablation coverage algorithm (e.g., by the system 10 of FIG. 1) is a practically realizable solution to cover the PTV. Some, but not all, aspects of the coverage algorithm described in FIGS. 1-10 require the movement of a set of ablations towards a single point or a set of attractor points to minimize the number of ablations as well as the collateral damage to healthy tissue. An ablation is moved to a new proposed location and a test is performed to determine whether the complete set of ablations (after the adjustment) continue to cover the PTV. The simple act of moving the center of an ellipsoidal ablation to a proposed center requires the coverage algorithm to recompute all voxels that are covered by the ablation at the proposed center. This is an important step in the coverage algorithm.

While various aspects of the algorithms described with regard to FIGS. 1-10 compute the voxel coverage of an ellipsoid that is centered at a proposed ablation center but retain the two independent orientation angles ($\theta$ and $\phi$) the same for all ablations, keeping the orientation angles the same for all ablations simplifies the computation of the voxels covered by the ablation. Accordingly, the optimization component 14 (FIG. 1) can compute the voxel coverage of the ellipsoid with new orientation angles at each proposed ablation center. The new orientation angles are determined by a line joining the proposed ablation center to the fulcrum point determined at the outset of the ablation planning. As each ablation is considered for a movement (e.g., tightening) to the proposed center, the algorithm recomputes the new orientation angles and applies those angles to the computation of the voxels covered by the ablation. Thus, the orientation of an ablation is ablation location-dependent and not simply a property of the location of the skin entry point and PTV centroid.

In one embodiment, the systems and methods of FIGS. 1-10 are used to compute a minimal number of ablations for covering an arbitrarily-shaped PTV volume with multiple identically-sized ellipsoidal ablations. However, such systems and methods are adapted so that the ablations are allowed to have a variable orientation as determined by the line joining the ablation center to the fulcrum point.

In another embodiment, a user segments the planned target volume (e.g., the user determines the contours of the PTV in each slice of the anatomical image dataset), selects a pre-specified RFA needle or explicitly specifies the exact shape of the ellipsoidal ablation created by a RFA needle in terms of radii along three orthogonal axes, and places a needle entry point (or a fulcrum point) on the skin surface. The user-specified entries contribute to the inputs for executing the ablation coverage algorithm.

The ablation coverage algorithm FIG. 5 is executed with user-specified inputs. In step 86 of FIG. 5, the unique coverage area (e.g., voxels covered by the ablation at a proposed center) is determined. In an alternative embodiment, this step is modified as follows: a line that joins the fulcrum point to the proposed ablation center is generated. The orientation of this line in the frame of reference is computed using the external 3D coordinate system in which the ablation centers are being computed. The orientations consist of two angles, theta ($\theta$) and phi ($\phi$), which are computed as follows. The projection of the line onto the X-Y plane and the angle subtended by the projected line from the positive X axis along the X-Y plane are computed to form the angle $\theta$. The projection of the line onto the X-Z plane and the angle subtended by the projected line from the positive Z axis along the X-Z plane are computed to form the angle $\phi$. The ellipsoidal ablation shape is then computed at the proposed center (x0, y0, z0) using the three ablation radii (a, b, c), and the computed orientation angles, theta ($\theta$) and phi ($\phi$). A voxel at location (x,y,z) is considered inside the ablation if it satisfies the ellipsoid equation. Transformation matrices (Txy, Txz) are employed to convert 3D points in the external coordinate system to the local coordinate system referenced to the center of the ablation, such that:

$$\frac{x'^2}{a^2} + \frac{y'^2}{b^2} + \frac{z'^2}{c^2} \leq 1.0, \text{ where}$$

$$\begin{pmatrix} x' \\ y' \\ z' \end{pmatrix} = T_{xy} T_{xz} \begin{pmatrix} x - x_0 \\ y - y_0 \\ z - z_0 \end{pmatrix}$$

$$T_{xy} = \begin{pmatrix} \cos\theta & \sin\theta & 0 \\ -\sin\theta & \cos\theta & 0 \\ 0 & 0 & 1 \end{pmatrix}$$

$$T_{xz} = \begin{pmatrix} \cos\phi & 0 & \sin\phi \\ 0 & 0 & 0 \\ -\sin\phi & 0 & \cos\phi \end{pmatrix}$$

The algorithm assigns all voxels within a rectangular bounding box around the proposed ablation center as either lying inside or outside the ablation. This new voxel coverage calculation is used within the algorithm computation. In this manner, the algorithm computes the ablation centers and orientations for a minimal set of ablations that completely cover the PTV and also minimizes the collateral damage.

In one embodiment, the algorithm (e.g., via the planning system 10 of FIG. 1) reports the number of ablations, the collateral damage, the visualization of the entry point, the PTV and composite ablation volume (union of all the voxels that are ablated by all the individual ablations), the centers of each of the ablations, and the orientation of each ablation as determined by the algorithm.

FIG. 22 illustrates an example of an irregular ablation 250, such as may occur when using a conventional ablation probe tip 122. Ablations are typically not perfectly elliptical in shape. This occurs for a variety of reasons: devices may have multiple tines, such as the LeVeen™ ablation device, creating a mushroom shape; actual ablation shapes may be affected by blood flow, which acts as a heat sink, competing with the heat from the RF ablation probe; "elliptical" devices are not perfectly ellipsoidal, they are approximated; etc.

Whenever there is an approximation, the possibility of under-treatment arises (which can be lethal), or over-treatment, which might mean that a procedure takes longer than necessary and in the extreme situation, may mean that a treatable patient is deemed ineligible for treatment (perhaps due to inability to tolerate anesthesia for the required time, etc.).

There are myriad issues to consider when planning an ablation procedure. For instance, success rate drops dramatically once a lesion is large enough so that it cannot be covered easily by a single ablation. Ablation must completely cover all tumor cells. Leaving any portion of the tumor untreated causes a recurrence, often an aggressive recurrence. Determining the coverage plan involves complex 3D geometric calculations and visualization which can be difficult for even the best of physicians. Each additional (15 minute) ablation adds to the surgical and anesthesia time and cost and increases risk to the patient.

Additionally, mental visualization of a single target location in 3-space can be complicated. Controlling a probe so that it accurately reaches that location adds additional potential for error. Ablation shapes often do not match the shape or size of the tumor, causing ablation of healthy tissue surrounding the tumor. Ablations may also damage 'critical regions' that can cause serious injury to the patient. Probe entry angles are often chosen because they match the imaging system rather than because they minimize the number of ablations or reduce procedure risk. Since each physician mentally creates a picture and plan, and hand-directs the probe, there is little chance for repeatability, which is important for evidence based medicine.

Accordingly, in one embodiment, the systems and methods described herein employ complex ablation shapes estimated by models rather than ellipsoids. A test burn or ablation can be performed to identify the precise shape of the ablation for a give probe tip 122. The 'true' ablation shape is then represented as a template volume representing coverage, and stored in the memory 20 of FIG. 1. The discretization of the ablation can be stored or quickly calculated as a function of the centroid and orientation of the ablation. For example, a mesh surface representation of the true ablation can be rotated and translated (e.g., by the processor 21 of the system 10) to define the specific coverage area of the ablation volume 250. Algorithmically, the voxels enclosed by the mesh replace the instances of "ellipsoid" in the algorithms described with regard to FIGS. 2, 5, and 10.

Further, rules of thumb, heuristics, as well as mathematical or experimental models can be employed (e.g., by the processor of FIG. 1) to make predictions about ablation shapes based on nearby blood flow that acts as a heat sink, which can remove or alter a section of the ablation shape depending on how close the ablation is to the vessel, as well as the pulse and blood flow.

FIGS. 23 and 24 illustrate a bounding polyhedron 270 and a PTV 240, respectively. The bounding polyhedron (in this example, a cube) includes a plurality of sides 272, each of which has a center 274, and is an example of a polyhedron that may be used to identify ablation centroid positions 282 for a plurality of smaller ablations that make up an enclosing ablation volume used to ablate the PTV 240. The centroids 282 of each ablation sphere 280 are aligned to the centers 274 of each side 272 of the bounding polyhedron 270 in order to ensure coverage of the PTV 240.

When selecting a polyhedron shape for a particular ablation situation, information including the desired PTV and ablation volume, where the PTV includes both the tumor and safety margin, is employed. Using only the relationship between the target and ablation radius, called the TA-Factor, the appropriate inscribing shape can be selected. Table 1 illustrates values for the shapes that are the most clinically useful for 15 minute-per ablation procedures:

TABLE 1

| TA-Factor = $PTV_{Radius}/Ablation_{Radius}$ | # Spherical Ablations required to cover. (Equals # sides of shape to right). | Shape inscribed in PTV sphere |
| --- | --- | --- |
| 1 | 1 | Point at center of PTV |
| 3/sqrt(8) ≅ 1.06 | 4 | Tetrahedron |
| sqrt(3)/sqrt(2) ≅ 1.2247 | 6 | Cube |
| ≅1.64 | 12 | Dodecahedron |

In the following example, the cube 270 of FIG. 23 is used to determine the location of 6 spherical ablations 280, covering the radius of the PTV 240 that is up to 1.22 times the size of the ablation radius of an ablation probe being employed. Although perhaps initially counterintuitive, the largest sphere enclosed by N unit spheres does not increase smoothly as N increases. In fact, it often decreases, such as when N=2 or 3. Further, some polyhedra are "duals" of lower-sided polyhedra, which means they inscribe (cover) the same sized sphere. For example, an octahedron (8 faces), covers a sphere of the same size as a cube (6 faces). A icosahedron (20 faces) covers the same sphere as a dodecahedron (12 faces). When trying to minimize the number of ablations, the smaller-faced dual is selected. The locations determined for spherical coverage of spherical PTV will be scaled in a subsequent part of the algorithm to provide the gravity points used as attractors.

In accordance with other embodiments, the described systems are employed to execute one or methods for minimizing collateral damage to surrounding tissue during an ablation procedure. For instance, in accordance with one embodiment, given a PTV and a known ablation volume and shape, a bounding polyhedron is selected for the ablation, and the PTV is scaled to a constant size TA*a,b,c, where TA is the tumor-to-ablation factor, and a, b, and c are the dimensions of an elliptical ablation volume generated by a selected ablation probe. The center of the enclosing ablation is positioned at the center of the bounding polyhedron (e.g., at coordinates A,B, C, where A=TA*a, B=TA*b, and C=TA*c), and thus at the center of the PTV. The TA factor is then increased until K*a>A, K*b>B and K*c>C.

Based on the TA factor, associated pre-computed points for the ablation centers are selected. For instance, if the nominal ablation sphere has dimensions (a,b,c)=(1,1,1) and the pre-computed points for coverage are P1, . . . , Pn, then the x,y,z locations for the pre-computed points (e.g., voxels) are rescaled by TA*a, TA*b, and TA*c, respectively.

In another embodiment, the known ellipsoidal ablation shape generated by the selected ablation probe tip is scaled to a round size by scaling upward ablation volume dimensions until all ablation volume dimensions are equal to the larges dimension of the original elliptical ablation volume. For instance, where an elliptical ablation volume has dimensions a>b,c, where a is a longitudinal axis of the ellipsoid, dimensions b and c are increased until they are equal to a and the volume is spherical. The dimensions of the spherical ablation volume may be denoted A,A,A for this example. The PTV is then scaled up by the same amount in respective directions. Optionally, a double-check may be quickly performed to make sure that each voxel or point's x,y,z coordinates (e.g., in the enclosing ablation volume) are multiplied by a, a/b, and a/c respectively.

The PTV is then circumscribed with the enclosing sphere, and the TA factor is determined, which describes the number of smaller ablations theoretically required to cover the larger enclosing ablation. Based on the TA factor, associated pre-computed points for the ablation centers are selected. For instance, if the nominal ablation sphere has dimensions (a,b, c)=(1,1,1) and the pre-computed points for coverage are P1, . . . , Pn, then the x,y,z locations for the pre-computed points (e.g., voxels) are each rescaled by TA*A. The smaller spherical ablations are then rescaled back to their final locations.

In this manner, ellipsoidal ablation volumes are scaled to spherical volumes to facilitate finding an ablation solution in the spherical domain, which solution is then employed as input for related ablation planning systems and methods, such as those described above with regard to FIGS. 1-10.

It will be understood that the various algorithms, methods, and the like, described herein may be stored in a memory component (such as the memory 20 of FIG. 1) as a set of computer-executable instructions that are executed by one or more processors (such as the processor 21 of FIG. 1) to perform the various actions, etc., described herein. The memory 20 may be volatile or non-volatile memory, and may include one or more of read-only memory (ROM), random access memory (RAM), programmable read-only memory (PROM), erasable programmable read-only memory (EPROM), electronically erasable programmable read-only memory (EEPROM), flash memory, solid-state memory, variants of the foregoing, or any other type of memory suitable for storing computer-executable instructions for execution by the one or more processors.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A method for planning an ablation procedure to eliminate a tissue mass in a patient, including:
   identifying a tissue mass in the patient;
   generating an image representation of an initial planned target volume (PTV) encompassing the tissue mass;
   inscribing the initial PTV in a template ellipsoidal enclosing ablation volume;
   scaling minor axes of the template ellipsoidal enclosing ablation volume and the initial PTV upward until they are equal in magnitude to a major axis of the template ellipsoidal enclosing ablation volume, to generate an enclosing sphere that encompasses the scaled PTV;
   identifying in a lookup table a pre-computed ablation solution having a minimum number of spherical ablation regions that cover the enclosing sphere; and
   outputting to a user a graphical representation of the identified precomputed ablation solution overlaid on the sphere.

2. The method according to claim 1, further including:
   scaling the minor axes of the ablation regions and the scaled PTV downward to generate ellipsoidal ablation regions that encompass the initial PTV; and
   outputting to a user a graphical representation of the ellipsoidal ablation regions and the initial PTV.

3. The method according to claim 1, wherein the ellipsoidal enclosing ablation volume has common relative dimensions and orientation with the initial PTV.

4. The method according to claim 1, further including:
   determining a tumor-to-ablation (TA) scaling factor that defines the minimum number of spherical ablation regions that cover the enclosing sphere; and
   using the TA factor to identify the precomputed ablation solution.

5. The method according to claim 1, further including:
   combining ablation volumes in the precomputed ablation solution that share a common axis into at least one block of ablations that is executed using a pull-back ablation technique.

6. The method according to claim 1, further including:
   performing a pilot ablation;
   determining a shape of an ablation volume generated during the pilot ablation; and
   generating an ablation solution comprising a plurality of ablation volumes having the determined shape to cover the PTV.

7. A method for planning an ablation procedure to eliminate a tissue mass in a patient, including:
   identifying a tissue mass in the patient;
   generating an image representation of an initial planned target volume (PTV) encompassing the tissue mass;
   selecting a bounding polyhedron as a function of a tumor-to-ablation (TA) factor that describes a relationship between radius of a known ellipsoidal ablation volume radius and radius of the PTV;
   positioning the bounding polyhedron around the PTV;
   positioning an ellipsoidal ablation volume in the bounding polyhedron such that a center of the ellipsoidal ablation volume coincides with a center of the bounding polyhedron;
   increasing the TA factor by which axes of the ellipsoidal ablation volume are multiplied until the axes are equal to or greater than corresponding dimensions of the bounding polyhedron;
   identifying in a lookup table a pre-computed ablation solution having a minimum number of spherical ablation regions that cover the enclosing sphere; and
   outputting to a user a graphical representation of the identified precomputed ablation solution overlaid on the scaled PTV.

8. The method according to claim 7, further including:
   scaling the minor axes of the ablation regions and the scaled PTV downward to generate ellipsoidal ablation regions that encompass the initial PTV; and
   outputting to a user a graphical representation of the ellipsoidal ablation regions and the initial PTV.

9. The method according to claim 7, wherein the ellipsoidal ablation volume has common relative dimensions and orientation with the initial PTV.

10. The method according to claim 7, further including:
    combining ablation volumes n the precomputed ablation solution that share a common axis into at least one block of ablations that is executed using a pull-back ablation technique.

11. The method according to claim 7, further including:
    performing a pilot ablation;
    determining a shape of an ablation volume generated during the pilot ablation; and
    generating an ablation solution comprising a plurality of ablation volumes having the determined shape to cover the PTV.

12. A system for planning an ablation procedure for ablation of a tissue mass in a patient, including:
    a graphical user interface that presents a representation of the tissue mass to a user; and
    an optimization component that generates a planned target volume (PTV), which includes the tissue mass, receives image data related to the tissue mass, generates an enclosing ellipsoid ablation volume that encompasses the PTV, identifies a polyhedron shape that encompasses the enclosing ellipsoid, identifies a plurality of spheroid ablation regions to cover the enclosing ellipsoid having respective centroids positioned on centers respective sides of the polyhedron shape, executes a mathematical algorithm to lengthen an axis of the spherical ablation regions to form ellipsoid ablation regions therefrom, and outputs graphical information to the user displaying the ellipsoid ablation regions overlaid on the PTV.

13. The system according to claim 12, wherein the optimization component generates an initial list of candidate ablation regions, each having a characteristic point at which a probe associated with the ablation component is positioned to treat a portion of the tissue mass in each ablation region, and determines a unique coverage area (UCA) for a predetermined number of candidate ablation regions such that the UCA for a given candidate ablation region includes a portion of the PTV that is covered solely by the given candidate ablation region.

14. The system according to claim 13, wherein the optimization component removes a candidate ablation region from the list of candidate ablation regions if the candidate ablation region does not have a UCA, executes a binary search algorithm to determine whether the characteristic points of the given candidate ablation region can be moved closer to a centering point of the PTV without compromising coverage of the UCA of the given candidate ablation region, and continues to optimize the model for tumor mass ablation until no candidate ablation region can be moved closer to the centering point and all UCAs are covered.

15. The system according to claim 12, wherein the optimization component executes a ray marching algorithm to generate at least one candidate insertion point on the skin of the patient, through which an ablation probe associated with the ablation component is inserted along a trajectory to the PTV while avoiding one or more critical regions.

16. The system according to claim 12, wherein the optimization component includes:
   a routine that selects an initial set of candidate ablation regions that cover a planned target volume (PTV);
   a routine that selects a centering point of the PTV;
   a routine that determines whether one or more candidate ablation regions in the initial set of candidate ablation regions remain to be evaluated;
   a routine that selects a candidate ablation region and evaluates a unique coverage area (UCA) there for;
   a routine that determines whether the UCA for the candidate ablation region is equal to zero;
   a routine that removes the candidate ablation region from the initial set of candidate ablation regions if the UCA is equal to zero;
   a routine that identifies a closest position to the centering point, to which the candidate ablation region is moved, while still covering the UCA, if the UCA is not equal to zero;
   a routine that determines that all candidate ablation regions are ready for reevaluation if one or more candidate ablation regions has been moved closer to the centering point; and
   a routine that causes all candidate ablation regions to be reevaluated.

17. The system according to claim 12, wherein the optimization component:
   optimizes an ablation plan as a function of at least one of functional data associated with the mass, location of one or more heat sinks near the tissue mass, a shape of an ablation probe selected to perform the ablation, a size of the ablation probe selected to perform the ablation, and a number of different ablation probes utilized during ablation;
   optimizes an ablation plan as a function of at least one of candidate ablation points, ablation probe entry angles, ablation temperature, ablation time, and critical regions; and
   utilizes a priori knowledge of at least one of a proximity of a PTV to a critical region, an ablation time associated with a selected ablation probe, an ablation temperature associated with the selected ablation probe, and one or more heat sinks located near the PTV.

18. The system according to claim 12, wherein the optimum number of ablation regions is a minimum number of ablation regions that covers the tissue mass, and wherein a user inputs a planned target volume (PTV), which encompasses the tissue mass, by outlining boundaries on one or more different views of the representation of the tissue mass, and the optimization component generates 3D voxels representing the planned target volume.

* * * * *